US007340485B2

(12) United States Patent
Varpela et al.

(10) Patent No.: US 7,340,485 B2
(45) Date of Patent: Mar. 4, 2008

(54) INFORMATION MANAGEMENT SYSTEM FOR BIOCHEMICAL INFORMATION

(75) Inventors: Pertteli Varpela, Espoo (FI); Meelis Kolmer, Espoo (FI)

(73) Assignee: Medicel Oy, Helsinki (FI)

( * ) Notice: Subject to any disclaimer, the term of this patent is extended or adjusted under 35 U.S.C. 154(b) by 460 days.

(21) Appl. No.: 10/883,036

(22) Filed: Jul. 2, 2004

(65) Prior Publication Data

US 2005/0010372 A1 Jan. 13, 2005

(30) Foreign Application Priority Data

Jul. 4, 2003 (FI) ................................. 20031020

(51) Int. Cl.
*G06F 17/30* (2006.01)
*G06F 7/00* (2006.01)
(52) U.S. Cl. .................................... 707/104.1; 707/101
(58) Field of Classification Search ................ 707/101, 707/104.1
See application file for complete search history.

(56) References Cited

U.S. PATENT DOCUMENTS

| 5,930,154 | A | 7/1999 | Thalhammer-Reyero |
| 6,272,468 | B1 * | 8/2001 | Melrose .......................... 705/2 |
| 6,553,317 | B1 | 4/2003 | Lincoln et al. |
| 2001/0023419 | A1 * | 9/2001 | Lapointe et al. .............. 706/15 |
| 2002/0187514 | A1 * | 12/2002 | Chen et al. ................... 435/7.1 |
| 2002/0194201 | A1 * | 12/2002 | Wilbanks et al. ......... 707/104.1 |
| 2003/0233218 | A1 * | 12/2003 | Schilling ...................... 703/11 |

FOREIGN PATENT DOCUMENTS

| WO | WO 99/66453 | 12/1999 |
| WO | 02/44992 A2 | 6/2002 |
| WO | WO 02/054188 A2 | 7/2002 |

OTHER PUBLICATIONS

Rojas et al.: "A database system for analysis of biochemical pathways", Dagstuhl Seminar "Functional Genomics", In Silico Biology 2, 0007 (2002), Bioinformation Systems, e.V.*

Goto, S. et al., "Organizing and computing metabolic pathway data in terms of binary relations," Institute for Chemical Research, Kyoto University (JAPAN), 12 pp, ( 1997).

(Continued)

Primary Examiner—Kuen S. Lu
(74) Attorney, Agent, or Firm—Barnes & Thornburg, LLP

(57) ABSTRACT

An information management system for managing biochemical information (200). The biochemical information (200) comprises data sets (202) and each data set comprises a variable value matrix containing variable values organized as rows and columns; a row description list, in a variable description language, of the rows in the variable value matrix; a column description list, in a variable description language, of the columns in the variable value matrix; and a fixed dimension description, in a variable description language, of one or more fixed dimensions that are common to all values in the variable value matrix. A benefit achieved by storing the numerical values as a scalar matrix is that the matrix can be analyzed with many commercially available data-mining tools, such as self-organizing maps or other clustering algorithms, that do not readily process dimensioned values.

12 Claims, 20 Drawing Sheets

OTHER PUBLICATIONS

Hucka, et a., "The System Biology Markup Language (SBML); a medium for representation and exchange of biochemical network models", Bioinformatics 2003 19: 524-531 (Mar. 1, 2003; http://bioinformatics.oupjournals.org/contents-by-date.2003.shtml, http://bioinformatics.oupjournals.org/content/vol19/issue4/index.shtml, http://bioinformatics.oupjournals.org/cgi/reprint/19/4/524.pdf).

Krishnamurthy, et al., "Pathways Database System: An integrated set of tools for biological pathways", SAC 2003, Mar. 9-12, 2003, Melbourne, Florida, USA (paper id #SACBIO-124).

Karp, "Pathway Database: A Case Study in Computational Symbolic Theories", Science, 293, 2001, pp. 2040-2044.

Rojas, Bernardi, Ratsch, Kania, Wittig, Saric, "A database system for the analysis of biochemical pathways", In silico Biology 2, 0007 (2002).

Reshetnikov, Karpov, Pot, Tereshchenko, "Vector PathBlazer: A New Pathway Analysis and Visualization Tool", ISMB 2003, 11th International Conference on Intelligent Systems for Molecular Biology, poster K-44, presented 30.6.2003.

Official Office Action dated Jun. 15, 2004, citing the attached references, in Finnish Patent Application No. FI 20031020, which is the application to which priority is claimed.

Goryanin et al., "Mathematical simulation and analysis of cellular metabolism and regulation" BIOINFORMATICS, Oxford University Press, Surrey, Great Britain, vol. 15, No. 9, Sep. 1999 pp. 749-758.

Schaf et al., "The Virtual Cell" Proceedings of the Pacific Symposium on Biocomputing, 1999, pp. 228-239.

Tomiya et al., "The E-Cell Project: Towards Integrative Simulation Of Cellular Processes", RECOMB 2000. Proceedings of the 4th. Annual International cConference on Computational Molecular Biology. Tokyo, Japan, Apr. 8-11, 2000, pp. 290-298.

\* cited by examiner

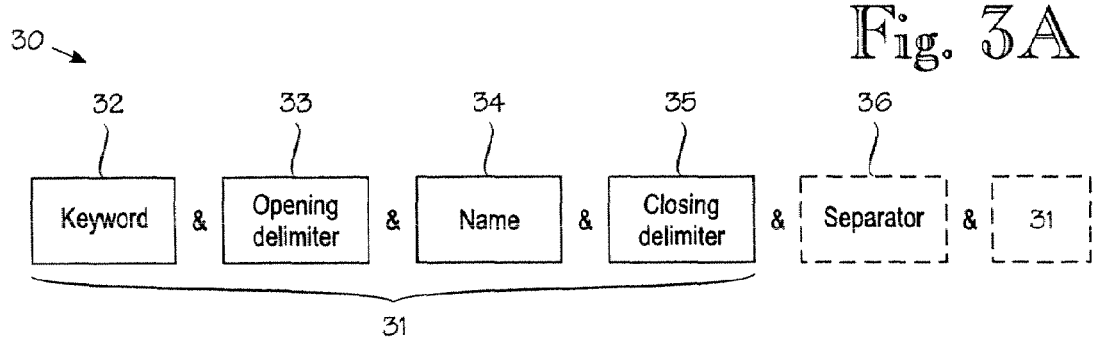

| | | |
|---|---|---|
| T | Time (relative) | T[-2.57E-3] |
| Ts | Time stamp | Ts[2002-11-26 14:00:00] |
| Sa | Sample | Sa[123456] |
| Po | Population | Po[2233445] |
| Id | Individual | Id[patient xyz] |
| Re | Reagent | Re[reagent a] |
| L | Location | L[yeast K2 mitocondria] |
| X/Y/Z | Spatial Z/Y/Z coordinate | X[0] relative to reference model |
| O | Organism | O[human] |
| V | Variable | V[concentration] |
| U | Unit | U[mol/l] |
| G | Gene | G[P53] |
| Tr | Transcript | Tr[mRNA from gene P53 to protein P53] |
| P | Protein | P[P53] |
| C | Compound | C[mannose] |
| M | Macromolecular complex | M[ribosome] |
| A | Abiotic stimuli | A[light] |
| I | Interaction | I[EC 1.2.3.4_P12345_F] |

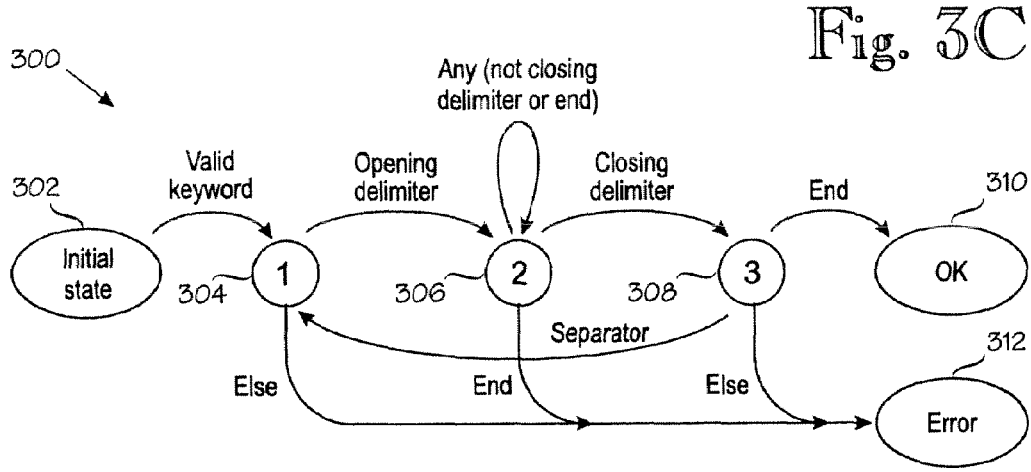

Fig. 3C

```
401 — V[concentration] of C[mannose]in U[mol/l]
402 — V[concentration] C[mannose]U[mol/l]
403 — V[concentration]of O[rat]P[P53] in U[mol/l]
404 — V[concentration] O[rat]P[P53] U[mol/l]
405 — V[concentration]of O[human]P[P53] in L[rat nucleus] in U[mol/l]
406 — V[concentration]O[human]P[P53] L[rat nucleus] U[mol/l]
407 — V[flux] of C[mannose]from I[EC 2.7.7.14 PSA1] in U[mol/l]
408 — V[flux]C[mannose]I[EC 2.7.7.14-PSA1]U[mol/l/s]
409 — V[reaction rate] through I[EC 2.7.7.14-PSA1] in U[mol/l/s]
410 — V[reaction rate]I[EC 2.7.7.14-PSA1]U[mol/l/s]
411 — I[EC 2.7.7.14-PSA1]
412 — V[flux] L[yeast golgi] C[mannose]I[mannose transport]U[mol/l/s]
414 — V[Expression level]Tr[mRNA from gene P53 to protein P53]U[-]
414 — V[*]P[*]O[*]L[*]U[*]
415 — Ts[2003.1.2 10:00:00, 2003.1.2 14:00:00]
417 — Ts[2003.1.2 12:00:00]T[-5,0, 5.0]
418 — L[human_eyelid_epith_nuc]
```

Fig. 4

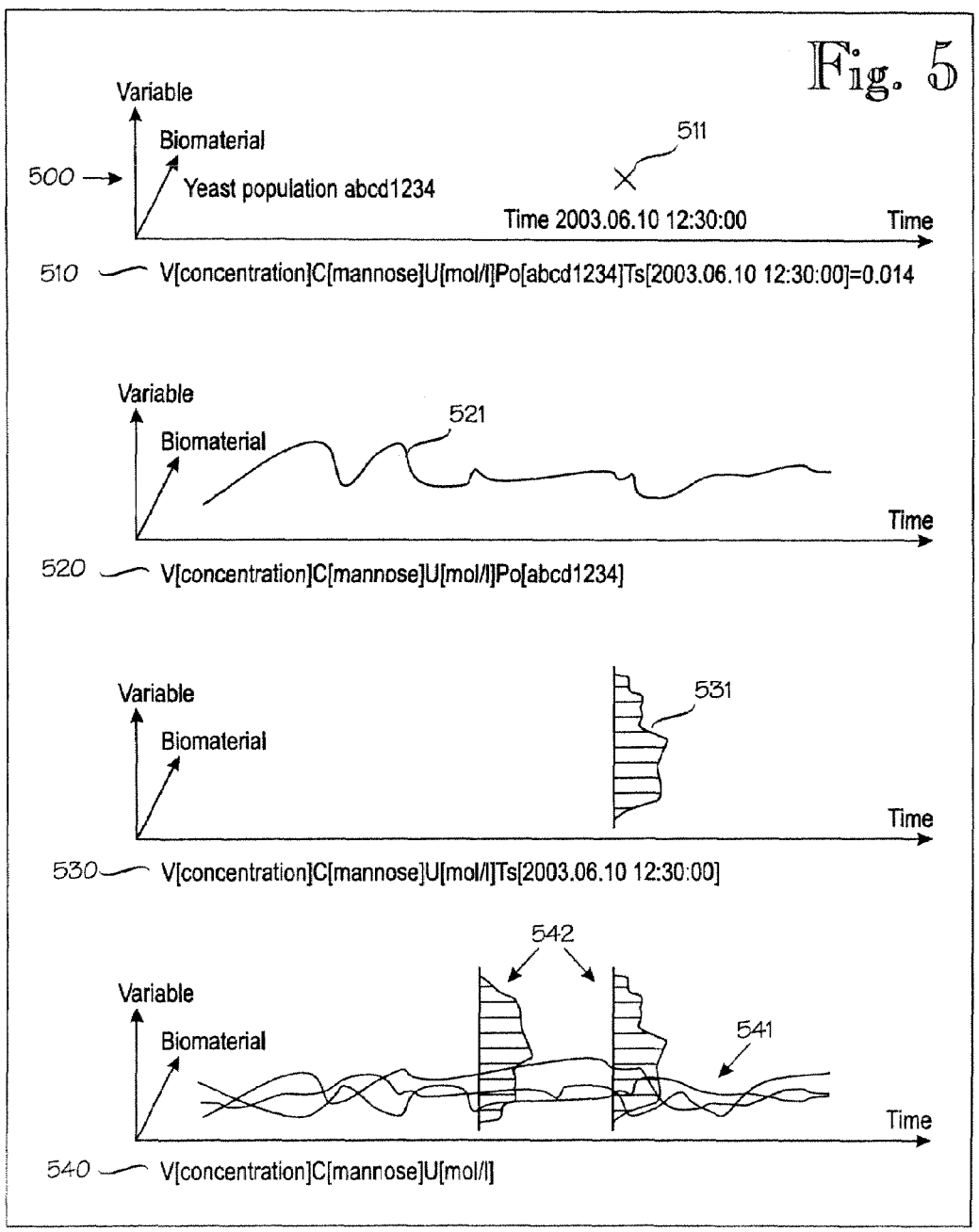

Fig. 6A

| Ts[*] | Id[patient A] | Id[patient B] | Id[patient C] | Id[patient D] |
|---|---|---|---|---|
| V[expression level]Tr[mRNA1...]U[-] | 25.18 | 40.83 | 39.46 | 28.15 |
| V[expression level]Tr[mRNA2...]U[-] | 9.76 | 15.45 | 14.91 | 11.84 |
| V[expression level]Tr[mRNA3...]U[-] | 250.66 | 99.43 | 546.23 | 429.00 |
| V[expression level]Tr[mRNA4...]U[-] | 99.02 | 75.39 | 88.25 | 94.67 |
| V[expression level]Tr[mRNA5...]U[-] | 3.07 | 9.45 | 10.23 | 6.78 |
| V[expression level]Tr[mRNA6...]U[-] | 101.12 | 210.85 | 124.92 | 145.63 |
| ... | ... | | | |
| V[age]U[years] | 67 | 81 | 75 | 62 |

```
Expression level of mRNA1 - mRNA6 of patients A - D at (time)
            A         B         C         D
mRNA1    25.18     40.83     39.46     28.15
mRNA2     9.76     15.45     14.91     11.84
mRNA3   250.66     99.43    546.23    429.00
mRNA4    99.02     75.39     88.25     94.67
mRNA5     3.07      9.45     10.23      6.78
mRNA6   101.12    210.85    124.92    145.63
           ...
age         67        81        75        62
```

Fig. 6B

| Po[Saccharomyces cerevisiae] Sa[xyz]Ts[2003.01.15 12:10:00] | T[0] | T[30] | T[60] | T[120] |
|---|---|---|---|---|
| V[expression level]Tr[mRNA1...]U[-] | 2.8 | 4.3 | 9.6 | 12.5 |
| V[expression level]Tr[mRNA2...]U[-] | 90.6 | 53.5 | 14.91 | 15.8 |
| V[expression level]Tr[mRNA3...]U[-] | 2500.6 | 1000.3 | 546.3 | 100.0 |
| V[expression level]Tr[mRNA4...]U[-] | 99.2 | 75.5 | 68.5 | 194.2 |
| V[expression level]Tr[mRNA5...]U[-] | 300.0 | 259.4 | 102.3 | 117.7 |
| V[expression level]Tr[mRNA6...]U[-] | 191.2 | 214.8 | 412.9 | 450.3 |
| ... | ... | | | |
| V[temperature]U[centigrade] | 25.0 | 30.1 | 35.0 | 39.8 |

Fig. 6C

| | Keyword | Value | Row | Column | (ObjectClass)/(ObjectID) |
|---|---|---|---|---|---|
| 631 { | Po | Saccharomyces cerevisiae | -1 | -1 | |
| | Sa | xyz | -1 | -1 | |
| | Ts | 2003.01.15 12:10:00 | -1 | -1 | |
| 633 { | V | expression level | 1-6 | -1 | |
| | Tr | mRNA1 | 1 | -1 | |
| | Tr | mRNA2 | 2 | -1 | |
| | Tr | mRNA3 | 3 | -1 | |
| | Tr | mRNA4 | 4 | -1 | |
| | Tr | mRNA5 | 5 | -1 | |
| | Tr | mRNA6 | 6 | -1 | |
| | U | - | 1-6 | -1 | |
| | V | temperature | 8 | -1 | |
| | U | centigrade | 8 | -1 | |
| 632 { | T | 0 | -1 | 1 | |
| | T | 30 | -1 | 2 | |
| | T | 60 | -1 | 3 | |
| | T | 120 | -1 | 4 | |

634  634A 634B 634C

| 1 | 1 | 2.8 |
|---|---|---|
| 1 | 2 | 4.3 |
| 1 | 3 | 9.6 |
| 1 | 4 | 12.5 |
| 2 | 1 | 90.6 |
| ... | | |
| 8 | 3 | 35.0 |
| 8 | 4 | 39.8 |

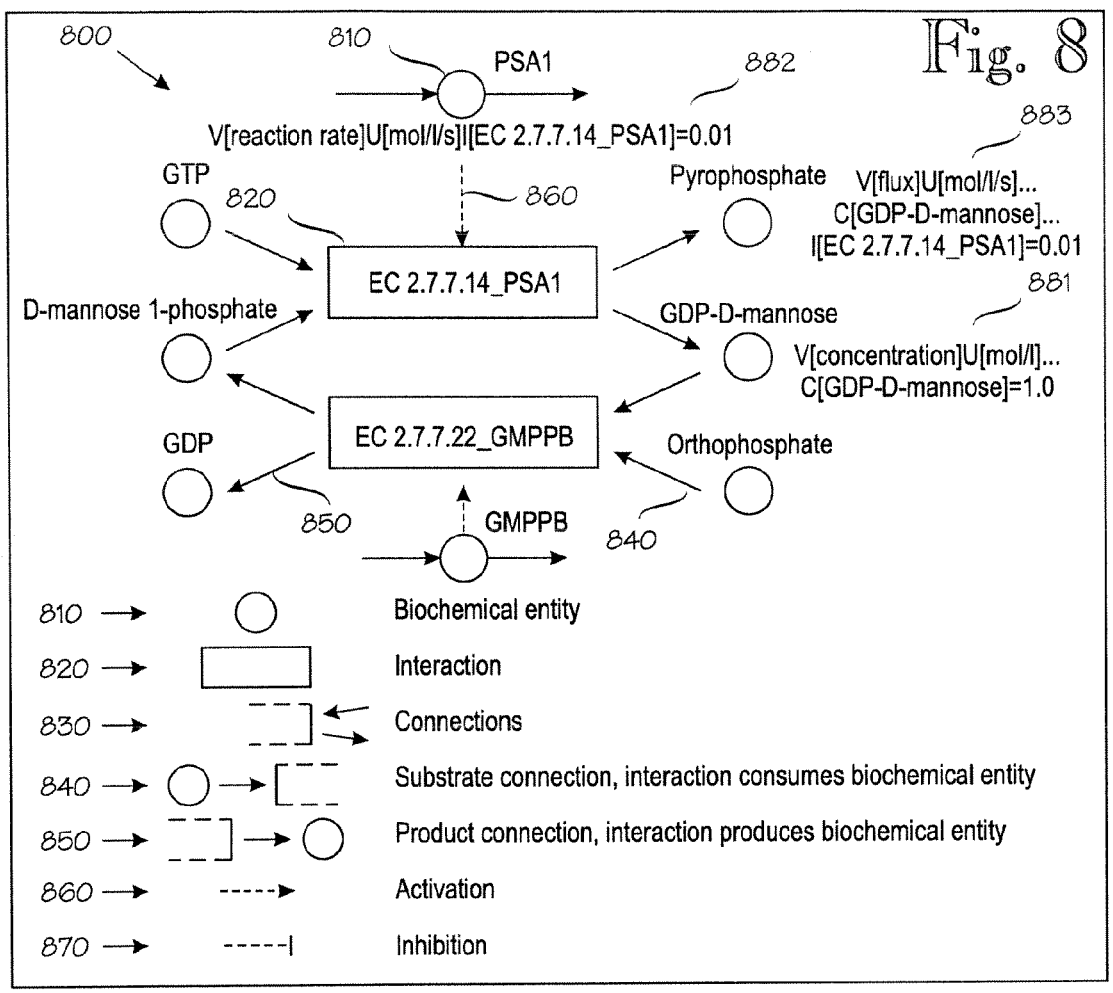
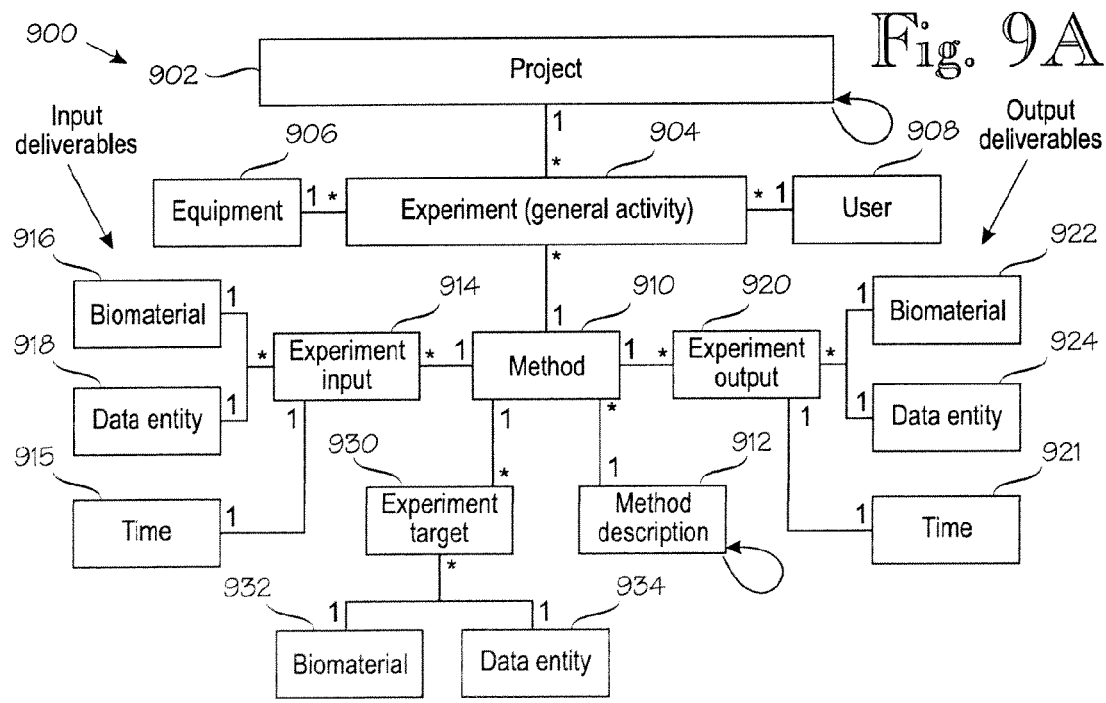

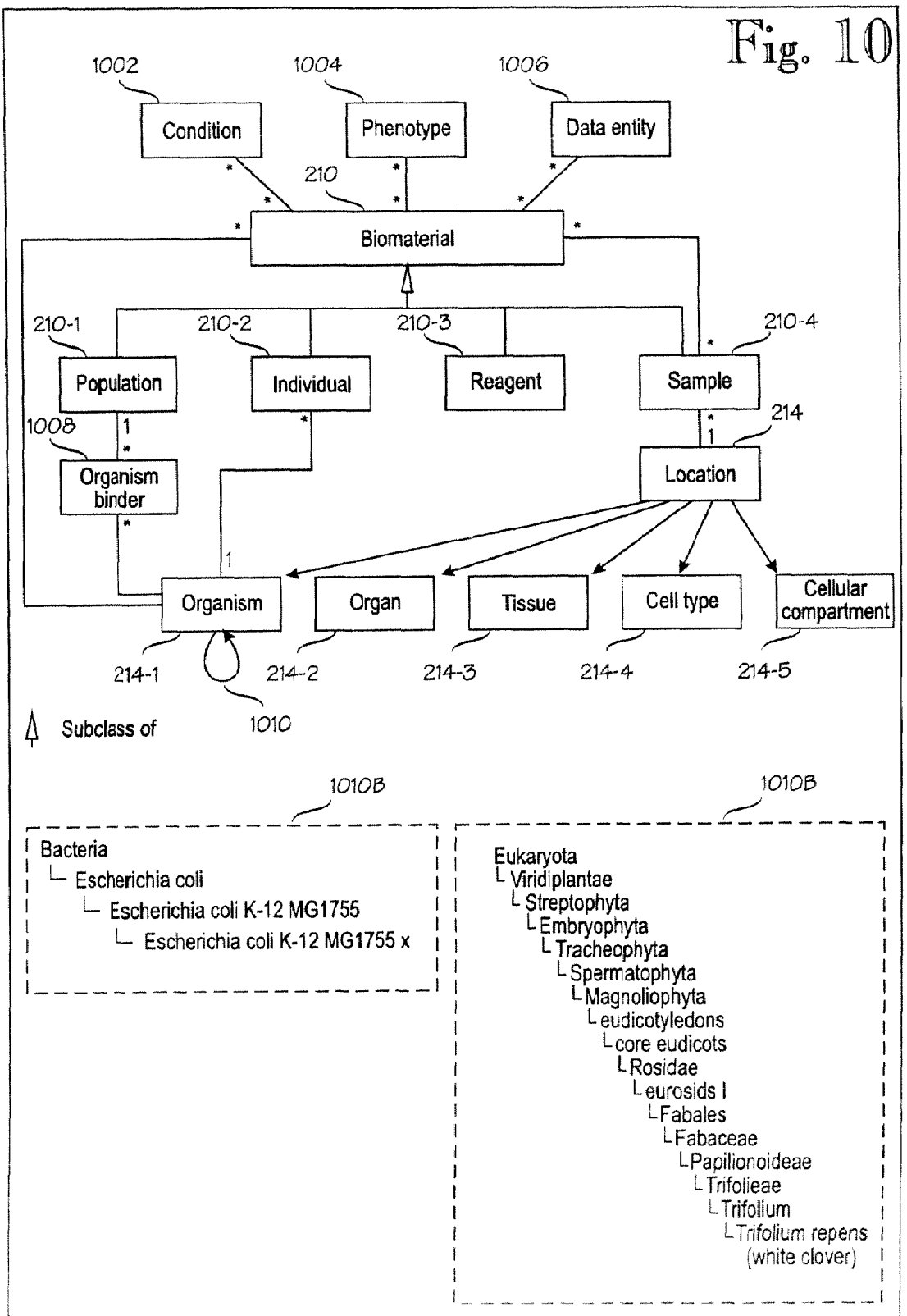

Fig. 16D

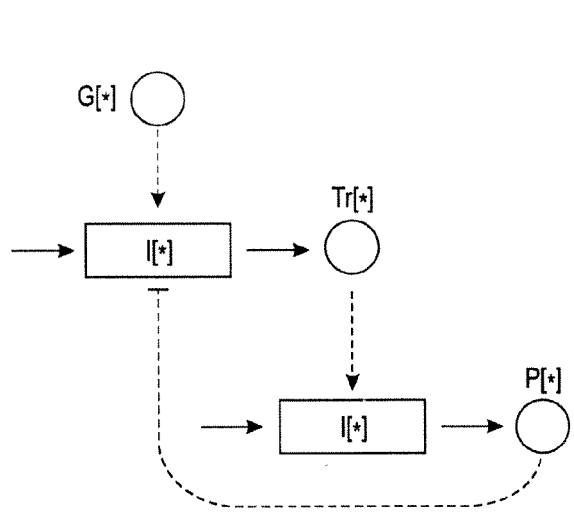

```
SELECT DISTINCT C1.id as C1_id, C2.id AS C2_id, C3.id AS C3_id, C4.id AS C4_id, C5.id AS C5_id
FROM connection C1, connection C2, connection C3, connection C4, connection C5
WHERE
C1.pathway_id = 2 AND
C2.pathway_id = 2 AND
C3.pathway_id = 2 AND
C4.pathway_id = 2 AND
C5.pathway_id = 2 AND
C1.type = 3 AND
C2.type = 2 AND
C3.type = 3 AND
C4.type = 2 AND
C5.type = 5 AND
C1.object_class = 'gene' AND
C2.object_class = 'transcript' AND
C3.object_class = 'transcript' AND
C4.object_class = 'protein' AND
C5.object_class = 'protein' AND
C2.object_id = C3.object_id AND
C4.object_id = C5.object_id AND
C1.interaction_id = C2.interaction_id AND
C3.interaction_id = C4.interaction_id AND
C5.interaction_id = C1.interaction_id AND
C5.interaction_id = C2.interaction_id
```

INFORMATION MANAGEMENT SYSTEM FOR BIOCHEMICAL INFORMATION

CROSS REFERENCE TO RELATED APPLICATIONS

This application claims the benefit of priority to Finnish Application 20031020 under 35 U.S.C. 119, filed on Jul. 4, 2003.

BACKGROUND OF THE INVENTION

The invention relates to an information management system ("IMS" in short) for managing biochemical information.

Biochemical research brings tremendous amounts of data at a rate which has never been seen in any discipline of science. A problem underlying the invention relates to the difficulties in organizing vast amounts of rapidly-varying information. IMS systems can be free-form or structured. A well-known example of a free-form IMS is a local-area network of a research institute, in which information producers (researches or the like) can enter information in an arbitrary format, using any of the commonly-available or proprietary applications programs, such as word processors, spreadsheets, databases etc. A structured IMS means a system with system-wide rules for storing information in a unified database.

A problem with a structured IMS is that it may not accommodate new types of information, or entering new types of information may require various work-around techniques. On the other hand, a free-format IMS suffers from the drawback that external knowledge may be needed to interpret the stored information. This means, for example, that a document of an experiment contains numerical values, but the full meaning of the numerical values and/or the arrangement of the experiment is not included in the document. Or, if the experiment is thoroughly documented, the document is likely to be very long and ambiguous.

BRIEF DESCRIPTION OF THE INVENTION

An object of the present invention is to provide an information management system (later abbreviated as "IMS") so as to alleviate the above disadvantages. The IMS should be logically complete so that as little external information as possible is needed to interpret the information contained in the IMS. In addition, the information contained in the IMS should be structured, so that the information can be accessed by a wide variety of information processing tools.

The object of the invention is achieved by an IMS which is characterized by what is stated in the independent claims. The preferred embodiments of the invention are disclosed in the dependent claims.

An IMS according to the invention may be used to store information about populations, individuals, reagents or samples of other biomaterials (anything that can be studied as a biological/biochemical system or its component). The IMS preferably comprises an experiment database. An experiment can be a real-life experiment ("wet lab") or a simulated experiment ("in-silico"). According to the invention, both experiment types produce structurally similar variable data sets, such that each variable data set comprises:

a variable value matrix for describing variable values in a row-column organization;

a row description list, in a variable description language, of the rows in the variable value matrix;

a column description list, in a variable description language, of the columns in the variable value matrix; and a fixed dimension description, in a variable description language, of one or more fixed dimensions that are common to all values in the variable value matrix.

The numerical values of each experiment are preferably stored as scalar (dimensionless) numbers in a variable value matrix having a row-column organization. Such row-column matrixes of scalar numbers can be further processed with a wide variety of off-the-shelf or proprietary application programs. There are separate row and column description lists for describing, respectively, the meaning of the rows and columns in the variable value matrix. A separate fixed dimension description describes the fixed dimensions that are common to all values in the variable value matrix. The row and column description lists, as well as the fixed dimension description, are written in a variable description language in order to link arbitrary variable values to the structured information of the IMS.

A benefit achieved by the use of the variable description language (=VDL) is that the IMS is largely self-sufficient. Little or no external information is needed to interpret the numerical values. Also, it is a relatively straightforward task to force an automated syntax check on the variable expressions. An essential feature of the VDL is that it permits the description of variables in varying detail level. For example, the VDL may describe what is quantified in terms of variables (eg count, mass, concentration), units (eg pieces, kg, mol/l), biochemical entities (eg a specific transcript, a specific protein or a specific compound). The VDL is also capable of specifying a specific location where the quantification is valid. The location may be expressed by biomaterial terms (eg environment, population, individual, reagent, sample, organism, organ, tissue, cell type) in a multi-level location hierarchy. The VDL is also capable of specifying absolute and relative times and time intervals. Thus the VDL is capable of expressing virtually any kind of biochemical information. On the other hand, details that are superfluous in a given context may be omitted.

XML (eXtendible Markup Language) is a well-known example of a language that can be used as a variable description language. A problem with XML is, however, that it is intended to describe virtually any kind of structured information, which results in lengthy expressions that are poorly readable by humans. Accordingly, a preferred embodiment of the invention relates to a variable description language that is better suited to describing biochemical variables than XML is. Also, expressions in XML and its biochemical or mathematical variants, such as SBML (Systems Biology Markup Language) or CellML (Cell Markup Language) or MathML (Mathematical Markup Language), are generally too long or complex to serve as self-documenting symbols for describing biochemical variables in mathematical models. Accordingly, a further preferred embodiment of the invention comprises a compact but extendible VDL that overcomes the problems of XML and its variants.

In a preferred implementation, the VDL is well-defined because only expressions that pass a syntax check shown in. The VDL is open because the permissible keywords are stored in an extendible table. The VDL is compact because substantially the minimum number of letters or characters are used for the keywords. Another reason for the compactness of the VDL described herein is that it does not require an explicit closing keyword for each opening keyword, which is typical of XML and its variants.

Yet another advantageous feature of the VDL described herein is that the keywords are not separated by paragraph (new line) characters, which is why most expressions require much less than a single line in a document or on a computer display.

A benefit achieved by storing the numerical values as a scalar matrix is that the matrix can be analyzed with many commercially available data-mining tools, such as self-organizing maps or other clustering algorithms, that do not readily process dimensioned values. Accordingly, the row and column descriptions are stored separately. A benefit achieved by the use of a third list, namely the fixed dimension description, is that dimensions common to rows and columns need not be duplicated in the row and column description lists.

The processing speed of the IMS can be increased by storing each data set (each data set comprising a variable value matrix, row and column description lists and a fixed dimension description) as a container for data, and storing only an address or identifier of the container in a database. Assuming that SQL (structured query language) or other database queries are used to retrieve the data sets, the single-container approach dramatically reduces the number of individual data items to be processed by SQL queries. When individual data elements are needed, the entire container can be processed with a suitable tool, such as a spreadsheet or flat-file database system.

An SQL-based implementation may be an advantageous way to internally represent this kind of data sets, however, particularly when data is sparse or there are redundant variable descriptions that can be stored efficiently by storing each data item only once in an appropriate data table.

A further advantage of the variable data sets according to the invention is good support for well-defined contexts. A context defines the scope of an experiment, either wet-lab or in-silico. Each context is defined in terms of biomaterials, variables and time.

According to another preferred embodiment of the invention, the IMS further comprises a biochemical entity database containing objects or tables. The variable description language comprises variable descriptions, each variable description comprising one or more pairs of keyword and name. For each object or table of the biochemical entity database, there is a keyword that references that object or table. This embodiment facilitates automated syntax or other checks made to information to be stored.

Another aspect of the invention is a method for storing biochemical information.

BRIEF DESCRIPTION OF THE DRAWINGS

In the following the invention will be described in greater detail by means of preferred embodiments with reference to the attached drawings, in which

FIGS. 3A and 3B illustrate a preferred variable description language, or VDL;

FIG. 3C illustrates a syntax-checking process for a variable expression in the VDL;

FIG. 4 shows examples of compound variable expressions in the VDL;

FIG. 5 shows how the VDL can be used to express different data contexts;

FIGS. 6A to 6C illustrate data sets according to various preferred embodiments of the invention;

FIG. 8 shows a visualized form of a pathway;

FIG. 9A shows an experiment object in an experiments section of the IMS;

FIG. 10 shows an example of an object-based implementation of the biomaterials section of the IMS;

FIGS. 16A to 16E illustrate pattern matching in searching for matching pathways.

DETAILED DESCRIPTION OF THE INVENTION

Figure 1:
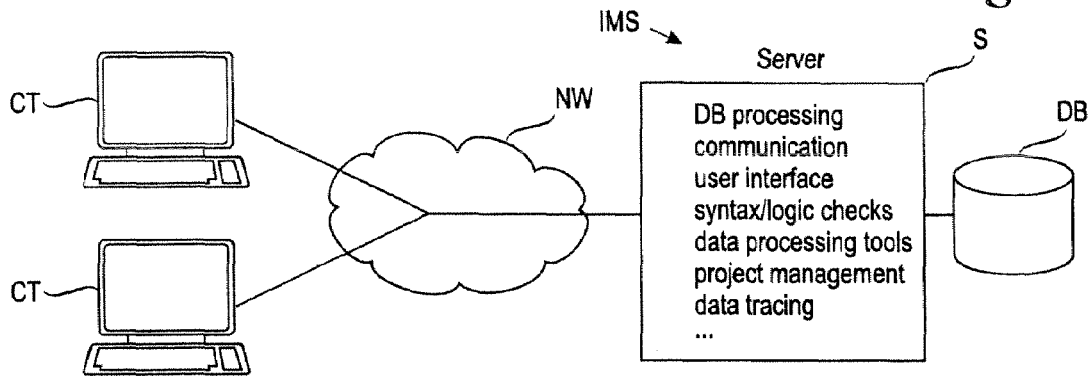
FIG. 1 is a block diagram of an IMS in which the invention can be used.

FIG. 1 is a simplified block diagram of an information management system IMS in which the invention can be used. In this example, the IMS is implemented as a client/server system. Several client terminals CT, such as graphical workstations, access a server (or set or servers) S via a network NW, such as a local-area network or the Internet. The server comprises or is connected to a database DB. The information processing logic within the server and the data within the database constitute the IMS. The database DB is comprised of structure and content. A preferred embodiment of the invention provides improvements to the structure of the database DB of the IMS. The server S also comprises various processing logics. A communication logic provides the basic server functions for communicating with the client terminals. There is preferably a user interface logic for creating various user interfaces. There may be various checks for checking the meaningfulness (such as syntax or range checks) of data to be entered. A very useful feature is a project manager with a tracing logic that provides visual tracing of data.

The server (or set of servers) S also comprises various data processing tools for data analysis, visualization, data mining, etc. A benefit of storing the data sets as containers in a row-column organization (instead of addressing each data item separately by SQL queries) is that such data sets of rows and columns can easily be processed with commercially available analysis or visualization tools. Before describing embodiments for the actual invention, i.e., the IMS for managing workflows and software tools, preferred embodiments for describing biochemical data will be described in connection with FIGS. 2 to 11B. Detailed embodiments of the IMS for managing workflows and software tools will be described in connection with FIGS. 12A to 18.

Data Sets

Figure 2:
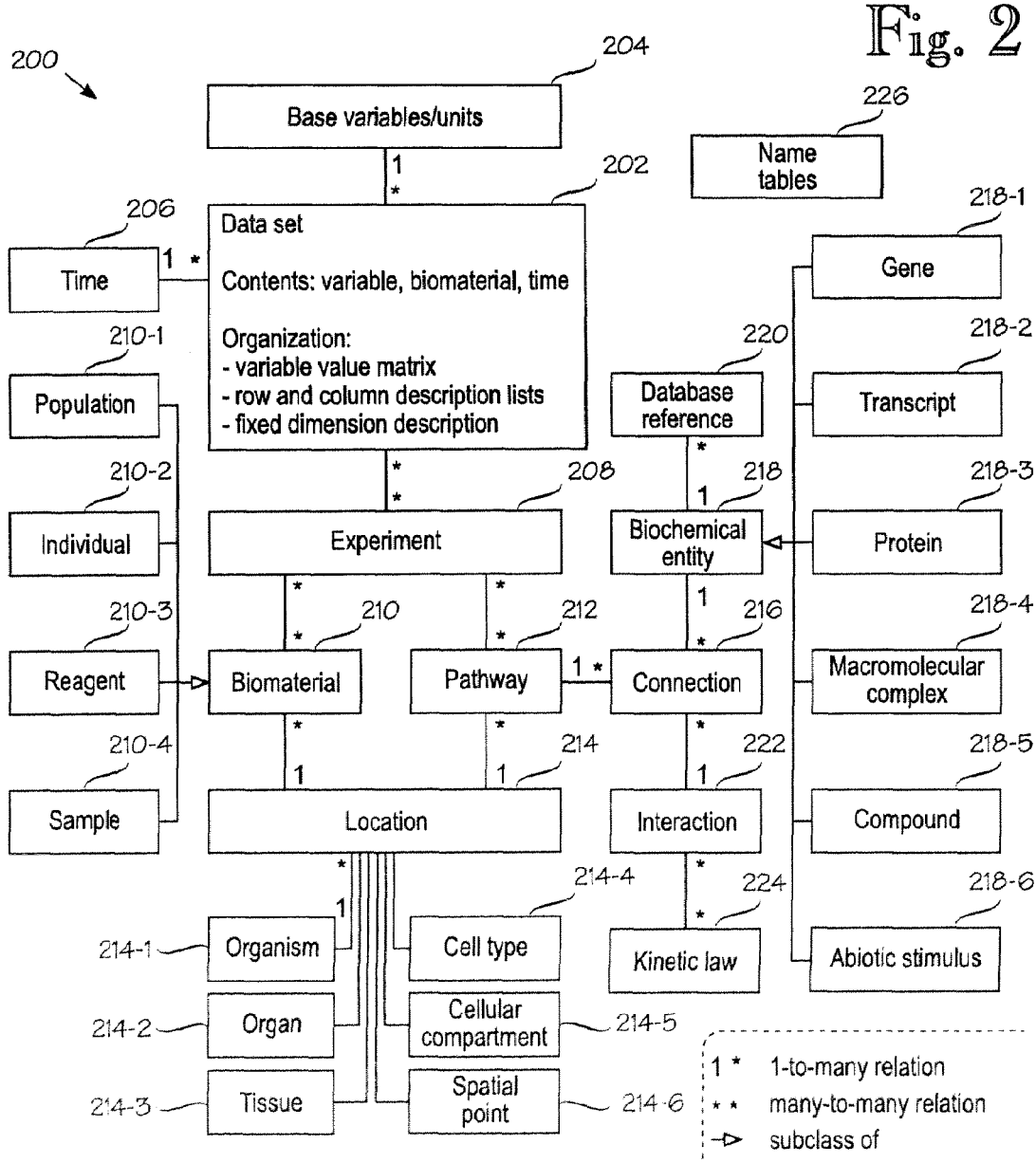
FIG. 2 is an entity-relationship model of a database structure of the IMS.

FIG. 2 is an entity-relationship model of a database structure 200 of the IMS. The database structure 200 comprises the following major sections: base variables/units 204, data sets 202, experiments 208, biomaterials 210, pathways 212 and, optionally, locations 214.

Data sets 202 describe the numerical values stored in the IMS. Each data set is comprised of a variable set, biomaterial information and time organized in
- a variable value matrix for describing variable values in a row-column organization;
- a row description list, in a variable description language, of the rows in the variable value matrix;
- a column description list, in a variable description language, of the columns in the variable value matrix; and
- a fixed dimension description, in a variable description language, of one or more fixed dimensions that are common to all values in the variable value matrix.

The variable description language binds syntactical elements and semantic objects of the information model together, by describing what is quantified in terms of variables (eg count, mass, concentration), units (eg pieces, kg, mol/l), biochemical entities (eg specific transcript, specific protein, specific compound) and a location where the quantification is valid (eg human_eyelid_epith_nuc) in a multi-level location hierarchy of biomaterials (eg environment, population, individual, reagent, sample, organism, organ, tissue, cell type) and relevant expressions of time when the quantification is valid.

Note that there are many-to-many relationships from the base variables/units section 204 and the time section 206 to the data set section 202. This means that each data set 202 typically comprises one or more base variable/units and one or more time expressions. There is a many-to-many relationship between the data set section 202 and the experiments section 208, which means that each data set 202 relates one or more experiments 208, and each experiment relates to one or more data sets 202. A preferred implementation of the data sets section will be further described in connection with FIGS. 6A to 6C.

The base variables/units section 204 describes the base variables and units used in the IMS. In a simple implementation, each base variable record comprises unit field, which means that each base variable (eg mass) can be expressed in one unit only (eg kilograms). In a more flexible embodiment, the units are stored in a separate table, which permits expressing base variables in multiple units, such as kilograms or pounds.

Base variables are variables that can be used as such, or they can be combined to form more complex variables, such as the concentration of a compound in a specific sample at a specific point of time.

The time section 206 stores the time components of the data sets 202. Preferably, the time component of a data set comprises a relative (stopwatch) time and absolute (calendar) time. For example, the relative time can be used to describe the speed with which chemical reactions take place. There are also valid reasons for storing absolute time information along with each data set. The absolute time indicates when, in calendar time, the corresponding event took place. Such absolute time information can be used for calculating relative time between any experimental events. It can also be used for troubleshooting purposes. For example, if a faulty instrument is detected at a certain time, experiments made with that instrument prior to the detection of the fault should be checked.

The experiments section 208 stores all experiments known to the IMS. There are two major experiment types, commonly called wet-lab and in-silico. But as seen from the point of view of the data sets 202, all experiments look the same. The experiments section 208 acts as a bridge between the data sets 202 and the two major experiment types. In addition to experiments already carried out, the experiments section 208 can be used to store future experiments. Preferred object-based implementations of experiments will be described in connection with FIG. 9A. A key design goal of the experiments section is data traceability as will be further described in connection with FIG. 11.

The biomaterial section 210 stores information about populations, individuals, reagents or samples of other biomaterials (anything that can be studied as a biochemical system or its component) in the IMS. Preferably, the biomaterials are described in data sets 202, by using the VDL to describe each biomaterial hierarchically, or in varying detail level, such as in terms of population, individual, reagent and sample. A preferred object-based implementation of the biomaterials section 210 will be described in connection with FIG. 10.

While the biomaterial section 210 describes real-world biomaterials, the pathway section 212 describes theoretical models of biomaterials. Biochemical pathways are somewhat analogous to circuit diagrams of electronic circuits. There are several ways to describe pathways in an IMS, but FIG. 2 outlines an advantageous implementation. In the example shown in FIG. 2, each pathway 212 comprises one or more connections 216, each connection relating to one biochemical entity 218 and one interaction 222.

The biochemical entities are stored in a biochemical entity section 218. In the example shown in FIG. 2, each biochemical entity is a class object whose subclasses are gene 218-1, transcript 218-2, protein 218-3, macromolecular complex 218-4 and compound 218-5. Preferably, there is an option to store abiotic stimuli 218-6, such as temperature, having potential connections to interactions and potential effects to relevant kinetic laws.

A database reference section 220 acts as a bridge to external databases. Each database reference in section 220 is a relation between an internal biochemical entity 218 and an entity of an external database, such as a specific probe set of Affymetrix inc.

The interactions section 222 stores interactions, including reactions, between the various biochemical entities. The kinetic law section 224 describes kinetic laws (hypothetical or experimentally verified) that affect the interactions. Preferred and more detailed implementations of pathways will be described in connection with FIGS. 7A, 7B and 8.

According to a preferred embodiment of the invention, the IMS also stores multi-level location information 214. The multi-level location information is referenced by the biomaterial section 210 and the pathway section 212. For instance, as regards information relating to biomaterials, the organization shown in FIG. 2 enables any level of detail or accuracy, from population level at one end down to spatial points (coordinates) within a cell at the other end. In the example shown in FIG. 2, the location information comprises organism 214-1 (eg human), organ 214-2 (eg heart, stomach), tissue 214-3 (eg smooth muscle tissue, nervous tissue), cell type 214-4 (eg columnar epithelium cell), cellular compartment 214-5 (eg nucleus, cytoplasm) and spatial point 214-6 (eg x=0.25, y=0.50, z=0.75 relative to the dimensions of a rectangular reference cell). The organism is preferably stored as a taxonomy tree that has a node to each known organism. The organ, tissue, cell type and cellular compartment blocks can be implemented as simple lists. A benefit of storing the location information as a reference to the predefined lists is that such referencing forces an automatic syntax check. Thus it is impossible to store a location information that references a non-existent or misspelled organ or organism.

According to a further preferred embodiment of the invention, the location information can also comprise spatial information 214-6, such as a spatial point within the most detailed location in the organism-to-cell hierarchy. If the most detailed location indicates a specific cell or cellular compartment, the spatial point may further specify that information in terms of relative spatial coordinates. Depending on cell type, the spatial coordinates may be Cartesian or polar coordinates. Spatial points will be further discussed in connection with FIG. 15.

In addition to the six levels of location hierarchy shown in FIG. 2, it is advantageous to add some more relations to the organism. Relations particularly advantageous with the organism include, from specific to generic: individual, population and environment. With this arrangement of levels, a biochemical entity (such as a sample) can be associated to virtually any location on earth, with any desired resolution, down to a specific spatial coordinate within a cell.

A benefit of this kind of location information is an improved and systematic way to compare locations of samples and locations of theoretical constructs like pathways that need to be verified by relevant measurement results.

The multi-level location hierarchy shown in FIG. 2 is particularly advantageous in connection with modern gene manipulation techniques, such as gene transfer and cloning. In comparison, some prior art systems label biological entities with simple text concatenations (such as "murine_P53"). Such a simple text concatenation hardcodes a specific organism to a specific location. If the location of the biological entity changes, its name changes as well, which disrupts the integrity of a well-defined database system. In contrast, the IMS as shown in FIG. 2 can easily identify a pig's P53 gene transplanted to a mouse, for example, or make a distinction between a parent organism and a cloned one.

Variable Description Language

FIGS. 3A to 3C illustrate a preferred variable description language, or "VDL". Generally speaking, a variable is anything that has a value and represents the state of a biochemical system (either a real-life biomaterial or a theoretical model). When an IMS is taken into use, the designer does not know what kinds of biomaterials will be encountered or what kinds of experiments will be carried out or what results are obtained from those experiments. Accordingly, variable descriptions have to be open to future extensions. On the other hand, openness and flexibility should not result in anarchy, which is why well-defined rules should be enforced on the variable descriptions. These needs are best served by an extendible variable description language ("VDL").

eXtendible markup language (XML) is one example of an extendible language that could, in principle, be used to describe biochemical variables. XML expressions are rather easily interpretable by computers. However, XML expressions tend to be very long, which makes them poorly readable to humans. Accordingly, there is a need for an extendible VDL that is more compact and more easily readable to humans and computers than XML is.

The idea of an extendible VDL is that the allowable variable expressions are "free but not chaotic". To put this idea more formally, we can say that the IMS should only permit predetermined variables but the set of predetermined variables should be extendible without programming skills. For example, if a syntax check to be performed on the variable expressions is firmly coded in a syntax check routine, any new variable expression requires reprogramming. An optimal compromise between rigid order and chaos can be implemented by storing permissible variable keywords in a data structure, such as a data table or file, that is modifiable without programming. Normal access grant techniques can be employed to determine which users are authorized to add new permissible variable keywords.

FIG. 3A illustrates a variable description in a preferred VDL. A variable description 30 comprises one or more pairs 31 of a keyword and name, separated by delimiters. As shown in the example of FIG. 3A, each keyword-name pair 31 consists of a keyword 32, an opening delimiter (such as an opening bracket) 33, a (variable) name 34 and a closing delimiter (such as a closing bracket) 35. For example, "Ts[2002-11-26 18:00:00]" (without the quotes) is an example of a time stamp. If there are multiple keyword-name pairs 31, the pairs can be separated by a separator 36, such as a space character or a suitable preposition. The separator and the second keyword-name pair 31 are drawn with dashed lines because they are optional. The ampersands between the elements 32 to 36 denote string concatenation. That is, the ampersands are not included in a variable description.

As regards the syntax of the language, a variable description may comprise an arbitrary number of keyword-name pairs 31. But an arbitrary combination of pairs 31, such as a concentration of time, may not be semantically meaningful.

FIG. 3B shows a table 38 of typical keywords. Next to each entry in table 38 is its plaintext description 38' and an illustrative example 38". Note that the table 38 is stored in the IMS but the remaining tables 38' and 38" are not necessarily stored (they are only intended to clarify the meaning of each keyword in table 38). For example the example for keyword "T" is "T[−2.57E−3]" which is one way of expressing minus 2.57 milliseconds prior to a time reference. The time reference may be indicated by a timestamp keyword "Ts".

The T and Ts keywords implement the relative (stopwatch) time and absolute (calendar) time, respectively. A slight disadvantage of expressing time as a combination of relative and absolute time is that each point of time has a theoretically infinite set of equivalent expressions. For example, "Ts[2002-11-26 18:00:30]" and "Ts[2002-11-26 18:00:00]T[00:00:30]" are equivalent. Accordingly, there is preferably a search logic that processes the expressions of time in a meaningful manner.

By storing an entry for each permissible keyword in the table 38 within the IMS, it is possible to force an automatic syntax check on variables to be entered, as will be shown in FIG. 3C.

The syntax of the preferred VDL may be formally expressed as follows:

```
<variable description>::=<keyword>"["<name>"]"
  {{separator}<keyword>"["<name>"]"}
  <end><keyword>::=<one of predetermined key-
  words, see eg table 38><name>::=<character
  string>|"*" for any name in a relevant data table
```

The purpose of explicit delimiters, such as "[" and "]" around the name is to permit any characters within the name, including spaces (but excluding the delimiters, of course).

A preferred set of keywords 38 comprises three kinds of keywords: what, where and when. The "what" keywords, such as variable, unit, biochemical entity, interaction, etc., indicate what was or will be observed. The "where" keywords, such as sample, population, individual, location, etc., indicate where the observation was or will be made. The "when" keywords, such as time or time stamp, indicate the time of the observation.

FIG. 3C illustrates an optional process for automatic syntax checking. A benefit of a formal VDL is that it permits an automatic syntax check. FIG. 3C illustrates a state machine 300 for performing such a syntax check. State machines can be implemented as computer routines. From an initial state 302 a valid keyword causes a transition to a first intermediate state 304. Anything else causes a transition to an error state 312. From the first intermediate state 304, an opening delimiter causes a transition to a second intermediate state 306. Anything else causes a transition to the error state 312.

After the opening delimiter, any characters except a closing delimiter are accepted as parts of the name, and the state machine remains in the second intermediate state 306. Only a premature ending of the variable expression causes a transition to an error state 312. A closing delimiter causes a transition to a third intermediate state 308, in which one keyword/name pair has been validly detected. A valid separator character causes a return to the first intermediate state 304. Detecting the end of the variable expression causes a transition to "OK" state 310 in which the variable expression is deemed syntactically correct.

FIG. 4 shows examples of compound variable expressions in the VDL. Compound variable expressions are expressions with multiple keyword/name pairs. Note how variables get more specific when qualifiers are added. Reference signs 401 to 410 denote five pairs of equivalent expressions such that the first expression of each pair is longer or more verbose and the second is more compact. For a computer, the verbose and compact expressions are equal, but human readers may find the verbose form easier to understand. By referencing table 38, the expressions in FIG. 4 are self-explanatory. For example, expressions 409 and 410 define reaction rate through interaction EC 2.7.7.13-PSA1 in moles per litre per second. Reference sign 414 denotes variable expression "V[*]P[*]O[*]U[*]" which means any variable of any protein of any organism in any units. Reference signs 415 and 416 denote two different variable expression for two different expressions of time. Variable expression 415 defines a three-hour time interval and variable expression 417 defines a 10-second time interval (beginning five seconds before and ending five seconds after the timestamp). Variable expression 418 is an expression of a hierarchical location expression. As shown in FIG. 2, the location information is preferably hierarchical and comprises database relations to organism 214-1, organ 214-2, tissue 214-3, cell type 214-4, cellular compartment 214-5 and/or spatial point 214-6, as appropriate. Variable expression 418 ("L[human_eyelid_epith_nuc]") is a visualized expression of such a multi-level hierarchical location information. Its organism relation 214-1 indicates a human, its organ relation 214-2 indicates eyelid, its cell type relation 214-4 indicates epithelial cell and its cellular compartment relation 214-5 indicates cell nucleus. In this example, the multi-level hierarchical location does not indicate any specific tissue or spatial point within the cell or cellular compartment.

Note that regardless of the language of humans using the IMS, it is beneficial to agree on one language for the variable expressions. Alternatively, the IMS may comprise a translation system to translate the variable expressions to various human languages.

The VDL substantially as described above is well-defined because only expressions that pass the syntax check shown in FIG. 3C are accepted. The VDL is open because the permissible keywords are stored in table 38 which is extendible. The VDL is compact because substantially the minimum number of letters or characters are used for the keywords. The most common keywords are comprised of a single letter, or two letters if a one-letter keyword is ambiguous. Another reason for the compactness of the VDL described herein is that it does not use keywords in pairs of opening keyword-closing keyword, such as "<ListOfProteins> . . . </ListOfProteins>", which is typical of XML and its variants. Yet another characteristic feature of the VDL described herein is that the keywords are not separated by paragraph (new line) characters, which is why most expressions require much less than a single line in a document or on a computer display. Actually, the inventive VDL does not require any separator characters (only closing delimiters, such as "]"), but separator characters, such as spaces or prepositions, may be used to enhance readability to humans.

Data Contexts

FIG. 5 shows how the VDL can be used to express different data contexts or scopes of biochemical research. All variables, whether sampled, measured, modelled, simulated or processed in any manner, can be expressed as:

a) single values for a biomaterial sample at a point of time;
b) functions of time for the biomaterial;
c) stochastic variables with their distributions at each point of time based on available biomaterial samples; or
d) stochastic processes in the biochemical data context.

a), b) and c) are projections of d) which is the richest representation of the system. All data in the IMS exists in a three-dimensional context space that has relations to:

1. list of variables ("what");
2. list of real-life biomaterials or pathway models ("where");
3. list of time points or time intervals ("when").

Reference numeral 500 generally denotes the N+2 dimensional context space having one axis for each of variables (N), biomaterials and time. A very detailed variable expression 510 specifies a variable (concentration of mannose in moles/l), biomaterial (population abcd1234) and a timestamp (10 Jun. 2003 at 12:30). The value of the variable is 1.3 moles/l. Since the variable expression 510 specifies all the coordinates in the context space, it is represented by a point 511 in the context space 500.

The next variable expression 520 is less detailed in that it does not specify time. Accordingly, the variable expression 520 is represented by a function 521 of time in the context space 500.

The third variable expression 530 does specify time but not biomaterial. Accordingly, it is represented by a distribution 531 of all biomaterials belonging to the experiment at the specified time.

The fourth variable expression 540 specifies neither time nor biomaterial. It is represented by a set 541 of functions of time and a set 542 of distributions for the various biomaterials.

By means of the various expressions made possible by the variable description language and suitably-organized data sets (to be described next), researchers have virtually unlimited possibilities to study the time-state space of a biochemical system as a multidimensional stochastic process. The probabilistic aspects of the system are based on the event space of relevant biomaterials, and the dynamic aspects are based on the time-space. Biomaterial data and time can be registered when the relevant experiments are documented.

All quantitative measurements, data analyses, models and simulation results can be reused in new analysis techniques to find relevant background information, such as phenotypes of measured biomaterials when the data needs to be interpreted for various applications.

Data Sets

FIGS. 6A to 6C illustrate data sets according to various preferred embodiments of the invention. Both wet-lab and in-silico experiment types are preferably stored as data sets of similar construction. By storing data related to wet-lab and in-silico experiments in similarly constructed data sets, it is possible to use output data from a wet-lab experiment as input data to an in-silico experiment, for example, without any intervening data format conversions. In FIG. 6A, an exemplary data set 610 describes expression levels of a number of mRNA molecules (mRNA1 through mRNA6 are shown). Data set 610 is an example of a data set stored in the data set section 202 shown in FIG. 2. The data set 610 comprises four matrixes 611 through 614. A variable value matrix 614 describes the values of the variables values in a row-column organization. A row description list 613 specifies the meaning of the rows of the variable value matrix. A column description list 612 specifies the meaning of the columns of the variable value matrix. Finally, a fixed dimension description 611 specifies one or more fixed dimensions that are common to all values in the variable value matrix 614. Note that the variable value matrix 614 is comprised of scalar numbers. The remaining matrixes 610 to 613 use the VDL to specify the meaning of their contents.

FIG. 6A also shows a human-readable version 615 of the data set 610. Note that the human-readable version 615 of the data set is only shown for better understanding of this embodiment. The human-readable version 615 is not necessarily stored anywhere, and can be created from the data set 610 automatically whenever a need to do so arises. The human-readable version 615 is an example of data sets, such as spreadsheet files, that are typically stored in prior art IMS systems for biochemical research. The IMS preferably contains a user interface logic for automatic two-way conversion between the storage format 611-614 and the human-readable version 615.

FIG. 6B shows another data set 620. The data set 620 also specifies expression levels of six mRNA molecules, but these are not expression levels of different individuals but of a single population at four different times. In the data set 620, the fixed dimension description 621 specifies that the data relates to sample xyz of a certain yeast at a certain date and time. The column description list 622 specifies that the columns specify data for four instances of time, namely 0, 30, 60 and 120 seconds after the time stamp in the fixed dimension description 621. The row description list 623 is very similar to the corresponding list 613 in the previous example, the only difference being that the last row indicates temperature instead of patient's age. The variable value matrix 624 contains the actual numerical values.

The division of each data set (eg data set 610) to four different components (the matrixes 611 to 614) can be implemented so that each matrix 611 to 614 is a separately addressable data structure, such as a file in the computer's file system. Alternatively, the variable value matrix can be stored in a single addressable data structure, while the remaining three matrixes (the fixed dimension description and the row/column descriptors) can be stored in a second data structure, such as a single file with headings "common", "rows" and "column". A key element here is the fact that the variable value matrix is stored in a separate data structure because it is the component of the data set that holds the actual numerical values. If the numerical values are stored in a separately addressable data structure, such as a file or table, it can be easily processed by various data processing applications, such as data mining or the like. Another benefit is that the individual data elements that make up the various matrixes need not be processed by SQL queries. An SQL query only retrieves an address or other identifier of a data set but not the individual data elements, such as the numbers and descriptions within the matrixes 611 to 614.

FIG. 6C shows an alternate implementation of the data sets. This implementation is particularly advantageous with sparse data or if there are redundant variable descriptions that can be stored efficiently by storing each data item only once in an appropriate data table. The example shown in FIG. 6C stores precisely the same data that was shown in FIG. 6B, but in a different organization. A variable value matrix 634 is a 3*n matrix, wherein n is the number of actual data items. The data items are stored in column 634C, which comprises precisely the same data as the variable value matrix 622 of FIG. 6B (although some elements are hidden, as indicated by the ellipsis). In addition to column 634C, the variable value matrix 634 comprises a row indicator column 634A and a column indicator column 634B, which indicate the row and column which the corresponding data item belongs to. The variable value matrix 634 is particularly advantageous when data is very sparse, because null entries need not be stored. On the other hand, the variable value matrix 634 requires explicit row and column indicators.

In the example of FIG. 6C, the significance of the data, ie, the row/column descriptors and the common descriptors are stored in a matrix or table 630, that has entries for keyword, value, row and column. Section 631 of the matrix 630 corresponds to the fixed dimension description 621 shown in FIG. 6B. The three elements in the fixed dimension description 621, ie, population, sample and time stamp, are stored as separate rows in section 631 of matrix 630. For instance, the first row has an entry of "Po" (=population) for the keyword, "*Saccharomyces cerevisiae*" for the corresponding value, and "−1" for each of the row and column. In this example, "−1" is a special value which is valid for all rows or column. As the section 631 is valid for all rows and columns, its contents correspond to the fixed dimension description 621 shown in FIG. 6B. Section 633 corresponds to the row description 623 of FIG. 6B. In section 633, the column indicators are "−1", which means "any column". The first line of section 633 means that the keyword "V" (=variable) and its value ("expression level") are valid for rows 1 to 6. The next six lines are six different row descriptors for rows 1 to 6, and so on. Finally, section 632 correspond to the column description 622 in FIG. 6B. Here, the rows are all "−1", since the column descriptors are valid for all rows.

The matrixes 630 and 634 shown in FIG. 6C comprise precisely the same information as the common and row/column descriptors 621 to 623 in FIG. 6B, as far as human readers are concerned. But interpretation of data by computers can be facilitated by storing separate entries for object class and object identifier. This feature eliminates some extra processing steps, such as data look-up via a keyword table 38 shown in FIG. 3B.

Pathways

Figure 7A:
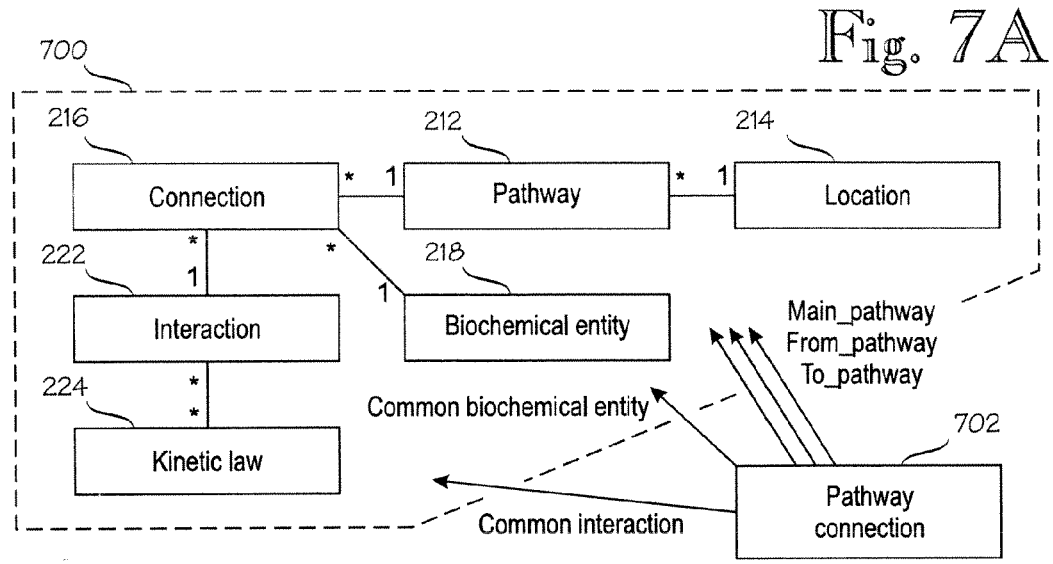
FIG. 7A is a block diagram of a pathway as stored in the IMS.

FIG. 7A is a block diagram of a pathway as stored in the IMS. An IMS according to a preferred embodiment of the invention describes each biochemical system by means of a structured pathway model 700 of system components and inter-component connections. The system components are biochemical entities 218 and interactions 222. The connections 216 between the biochemical entities 218 and interactions 222 are recognized as independent objects representing the role (eg substrate, product, activator or inhibitor) of each biochemical entity in each interaction for each pathway. A connection can hold attributes that are specific to each biochemical entity and interaction pair (such as a stoichiometric coefficient). As stated earlier, the IMS preferably stores location information, and each pathway 212 relates to a biological location 214. One biological location might be described by one or more pathways depending on the level of details that have been included into a pathway.

As shown in FIG. 7A, each connection 216 acts as a T joint that joins three elements, namely an interaction 222, a biochemical entity 218 and a pathway 212. In other words, the join of an interaction 222 and a biochemical entity 218 is pathway-specific, as opposed to global. This means that a biochemical researcher can change the interaction data relating to a given biochemical entity, and the change only affects the specific pathway indicated by the pathway element 212. This feature is believed to lower the psychological threshold faced by researchers to make changes to a pathway definition.

In an object-based implementation, the biochemical pathway model is based on three categories of objects: biochemical entities (molecules) 218, interactions (chemical reactions, transcription, translation, assembly, disassembly, translocation, etc) 222, and connections 216 between the biochemical entities and interactions for a pathway. The idea is to separate these three objects in order to use them with their own attributes and to use the connection to hold the role (such as substrate, product, activator or inhibitor) and stoichiometric coefficients of each biochemical entity in each interaction that takes place in a particular biochemical network. A benefit of this approach is the clarity of the explicit model and easy synchronization when several users are modifying the same pathway connection by connection. The user interface logic can be designed to provide easily understandable visualizations of the pathways, as will be shown in connection with FIG. 8.

The kinetic law section 224 describes theoretical or experimental kinetic laws that affect the interactions. For example, a flux from a substrate to a chemical reaction can be expressed by the following formula:

$$V = \frac{V\max \cdot [S] \cdot [E]}{K + [S]}$$

wherein V is the flux rate of the substrate, Vmax and K are constants, [S] is the substrate concentration and [E] is the enzyme concentration. The reaction rate through the interaction can be calculated by dividing the flux by the stoichiometric coefficient of the substrate. Conversely, each kinetic law represents the reaction rate of an interaction, whereby any particular flux can be calculated by multiplying the reaction rate by the stoichiometric coefficients of the particular connections. The above kinetic law as the reaction rate of interaction EC2.7.7.14_PSA1 in FIG. 8 can be expressed in VDL as follows:

$V[\text{rate}]I[EC2.7.7.14\_PSA1]=V\max\cdot V[\text{concentration}]$
$C[GTP]\cdot V[\text{concentration}]P[PSA1]/(K+V[\text{concentration}]C[GTP])$ The flux from interaction EC2.7.7.14_PSA1 to compound GDP-D-mannose can be expressed in VDL as follows:

$V[\text{flux}]I[EC2.7.7.14\_PSA1]C[\text{GDP-D-mannose}]$
$=c1\cdot V[\text{rate}]I[EC2.7.7.14\_PSA1]=V\max\cdot V[\text{concentration}]C[GTP]\cdot V[\text{concentration}]P[PSA1]/(K+V[\text{concentration}]C[GTP])$, where c1 is the stoichiometric coefficient of the connection from interaction EC2.7.7.14_PSA1 to compound GDP-D-mannose and c1=1. In the above example, the kinetic law is a continuous function of variables V[concentration]C[GTP] and V[concentration]P[PSA1]. In addition, a proper description of some pathways requires discontinuous kinetic laws.

Figure 7B:
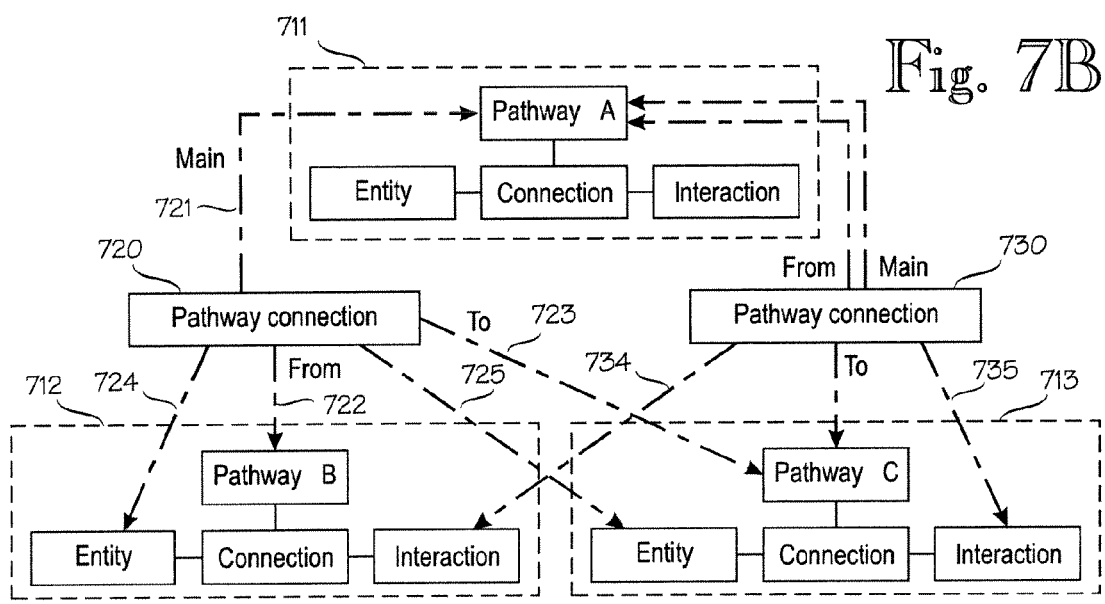
FIG. 7B shows an example of complex pathway that contains simpler pathways.
Figure 7C:
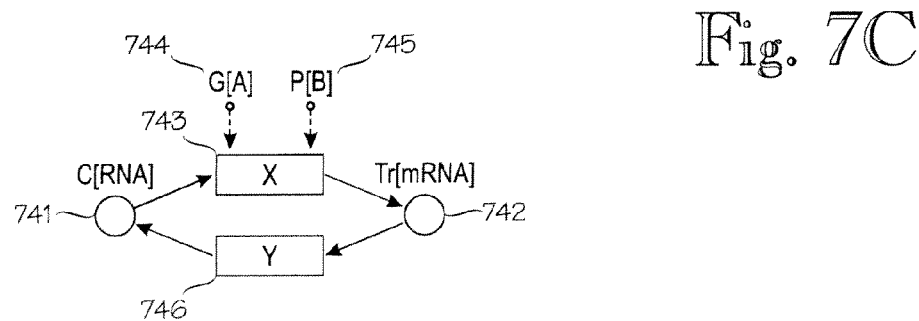
FIG. 7C shows an example of pathway that relates to analogue and Boolean flux rate equations.

FIG. 7C shows a visualized form of a hybrid pathway model that comprises both analogue (continuous) and Boolean (discrete) equations. In this model, compound RNA 741 is converted to transcript mRNA 742 via interaction (reaction) X 743 but only if gene A 744 and protein B 745 are present. Interaction Y 746 is the inverse process of interaction X 743 and transforms transcript mRNA back to compound RNA.

The kinetic law as the reaction rate of interaction X in FIG. 7C can be expressed as a discontinuous Boolean function of VDL conditions as follows:

V[rate]I[X]=k IF V[count]G[A]>0 AND V[count]P[B]>0 and V[count]C[RNA]>0 ELSE 0

The flux from interaction X to transcript mRNA can be expressed in VDL as follows:

$V[\text{flux}]I[X]Tr[\text{mRNA}]=c2\cdot V[\text{rate}]I[X]=k$ IF V[count]G[A]>0 AND V[count]P[B]>0 and V[count]C[RNA]>0 ELSE 0 where c2 is the stoichiometric coefficient of the connection from interaction X to transcript mRNA and c2=1.

Let the flux from interaction Y to compound RNA in FIG. 7C be a continuous function of the count of transcript mRNA as follows:

$V[\text{flux}]I[Y]C[RNA]=c3\cdot V[\text{rate}]I[Y]=c3\cdot k2\cdot V[\text{count}]Tr[\text{mRNA}]$ where c3 is the stoichiometric coefficient of the connection from interaction X to transcript mRNA and k2 is another constant of this kinetic law.

Each variable represented in the kinetic laws may be specified with a particular location L[ . . . ] if the concentration or count of a biochemical entity depends on a particular location.

A biochemical network may not be valid everywhere. In other words, the network is typically location-dependent. That is why there are relations between pathways 212 and biologically relevant discrete locations 214, as shown in FIGS. 1 and 7A.

A complex pathway can contain other pathways 700. In order to connect different pathways 700 together, the model supports pathway connections 702, each of which has up to five relations which will be described in connection with FIG. 7B.

FIG. 7B shows an example of complex pathway that contains simpler pathways. Two or more pathways can be combined if they have common biochemical entities that can move as such between relevant locations or common interactions (eg translocation type interaction that moves biochemical entities from one location to another). Otherwise, the pathways are considered isolated.

Pathway A, denoted by reference sign 711, is a main pathway to pathways B and C, denoted by reference signs 712 and 713, respectively. The pathways 711 to 713 are basically similar to the pathway 700 described above. There are two pathway connections 720 and 730 that couple the pathways B and C, 712 and 713, to the main pathway A, 711. For instance, pathway connection 720 has a main-pathway relation 721 to pathway A, 711; a from-pathway relation 722 to pathway B, 712; and a to-pathway relation 723 to pathway C, 713. In addition, it has common-entity relations 724, 725 to pathways B 712 and C 713. In plain language, the common-entity relations 724, 725 mean that pathways B and C share the biological entity indicated by the relations 724, 725.

The other pathway connection 730 has both main-pathway and from-pathway relations to pathway A 711, and a to-pathway relation to pathway C, 713. In addition, it has common-interaction relations 734, 735 to pathways B, 712 and C, 713. This means that pathways B and C share the interaction indicated by the relations 734, 735.

The pathway model described above supports incomplete pathway models that can be built gradually, along with increasing knowledge. Researchers can select detail levels as needed. Some pathways may be described in a relatively coarse manner. Other pathways may be described down to kinetic laws and/or spatial coordinates. The model also supports incomplete information from existing gene sequence databases. For example, some pathway descriptions may describe gene transcription and translation separately, while other treat them as one combined interaction. Each amino acid may be treated separately or all amino acids may be combined to one entity called amino acids.

The pathway model also supports automatic modelling processes. Node equations can be generated automatically for time derivatives of concentrations of each biochemical entity when relevant kinetic laws are available for each interaction. As a special case, stoichiometric balance equations can be automatically generated for flux balance analyses. The pathway model also supports automatic end-to-end workflows, including extraction of measurement data via modelling, inclusion of additional constrains and solving of equation groups, up to various data analyses and potential automatic annotations.

Automatic pathway modelling can be based on pathway topology data, the VDL expressions that are used to describe variable names, the applicable kinetic laws and mathematical or logical operators and functions. Parameters not known precisely can be estimated or inferred from the measurement data. Default units can be used in order to simplify variable description language expressions.

If the kinetic laws are continuous functions of VDL variables, the quantitative variables (eg concentration) of biochemical entities can be modelled as ordinary differential equations of these quantitative variables. The ordinary differential equations are formed by setting a time derivative of the quantitative variable of each biochemical entity equal to the sum of fluxes coming from all interactions connected to the biochemical entity and subtracting all the outgoing fluxes from the biochemical entity to all interactions connected to the biochemical entity.

Example:

$$\frac{dV[\text{concentration}]C[\text{GDP-D-mannose}]}{dV[\text{time}]} =$$

$$V[\text{flux}][EC\ 2.7.7.13\_PSA1]C[\text{GDP-D-mannose}] +$$

$$\ldots - V[\text{flux}]C[\text{GDP-D-mannose}][EC\ \ldots] - \ldots$$

$$\ldots$$

$$\frac{dV[\text{concentration}]C[\text{water}]}{dV[\text{time}]} =$$

$$V[\text{flux}]C[\text{water}][EC\ \ldots] + \ldots - V[\text{flux}]C[\text{water}][EC\ \ldots] - \ldots$$

On the other hand, if the kinetic laws are discontinuous functions of VDL variables, the quantitative variables (eg concentration or count) of biochemical entities can be modelled as difference equations of these quantitative variables. The difference equations are formed by setting the difference of the quantitative variable of each biochemical entity in two time points equal to the sum of the incoming quantities from all interactions connected to the biochemical entity and subtracting all the outgoing quantities from the biochemical entity to all interactions connected to the biochemical entity in the time interval between the time points of the difference.

Example:

$$V[\text{count}]Tr[mRNA]T[t + \Delta t] - V[\text{count}]Tr[mRNA]T[t] =$$

$$V[\text{flux}][X]Tr[mRNA] \bullet \Delta t - V[\text{flux}][Y]Tr[mRNA] \bullet \Delta t +$$

$$V[\ldots]\ldots - V[\ldots]\ldots$$

$$V[\text{count}]C[RNA]T[t + \Delta t] - V[\text{count}]C[RNA]T[t] =$$

$$V[\text{flux}][Y]C[RNA] \bullet \Delta t - V[\text{flux}][X]C[RNA] \bullet \Delta t +$$

$$V[\ldots]\ldots - V[\ldots]\ldots$$

If there are both continuous and discontinuous kinetic laws associated with an interaction that connects a biochemical entity, a difference equation is written from the biochemical entity such that continuous or discontinuous fluxes are added or subtracted depending on the direction of each connection.

In this way a complete "hybrid" equation system can be generated for simulation purposes with given initial or boundary conditions. Initial conditions and boundary conditions can be represented by the data sets described above (see FIGS. 6A to 6C).

In the differential and difference equations described above, the biochemical entity-specific fluxes can be replaced by reaction rates multiplied by stoichiometric coefficients.

In a static case, the derivatives and differences are zeros. This leads to a flux balance model with a set of algebraic equations of reaction rate variables (kinetic laws are not needed), wherein the set of algebraic equations describe the feasible set of the reaction rates of specific interactions.

$$0 = V[\text{rate}][EC\ 2.7.7.13\_PSA1] + \ldots - V[\text{rate}][EC\ \ldots] - \ldots$$

$$\ldots$$

$$0 = V[\text{rate}][EC\ \ldots] + \ldots - V[\text{rate}][EC\ \ldots] - \ldots$$

or $$0 = V[\text{rate}][X] - V[\text{rate}][Y] + V[\ldots]\ldots - V[\ldots]\ldots$$

$$0 = V[\text{rate}][Y] - V[\text{rate}][X] + V[\ldots]\ldots - V[\ldots]\ldots$$

Users can provide their objective functions and additional constraints or measurement results that limit the feasible set of solutions.

Yet another preferred feature is the capability to model noise in a flux-balance analysis. We can add artificial noise variables that need to be minimized in the objective function. The noise variables are given in the data sets described above. This helps to tolerate inaccurate measurements with reasonable results.

The model described herein also supports visualization of pathway solutions (active constraints). A general case, the modelling leads to a hybrid equations model where kinetic laws are needed. They can be accumulated in the database in different ways but there may be some default laws that can be used as needed. In general equations, interaction-specific reaction rates are replaced by kinetic laws, such as Michaels-Menten laws, that contain concentrations of enzymes and substrates. Example:

$$V[\text{reaction rate}]I[EC2.7.7.13\_PSA1]{=}5.2*V[\text{concentration}]P[PSA1]*V[\text{concentration}]C[\ldots]/(3.4+V[\text{concentration}]C[\ldots])$$

The equations can be converted to the form:

$$\frac{dV[\text{concentration}]C[GDP\text{-}D\text{-}mannose]}{dV[\text{time}]} =$$

$$5.2*V[\text{concentration}]P[PSA\text{-}1]^*V[\text{concentration}]C[\ldots]/$$

$$(3.4+V[\text{concentration}]C[\ldots])+$$

$$\ldots -7.9*V[\text{concentration}]P[\ldots]^*V[\text{concentration}]C[\ldots]/(\ldots)$$

$$\ldots$$

$$\frac{dV[\text{concentration}]C[\text{water}]}{dV[\text{time}]} =$$

$$10.0*V[\text{concentration}]P[\ldots]^*V[\text{concentration}]C[\ldots]/(\ldots)+\ldots -$$

$$8.6*V[\text{concentration}]P[\ldots]^*V[\text{concentration}]C[\ldots]/(\ldots)-\ldots$$

or $$V[\text{count}]Tr(mRNA)T[t+\Delta t] - V[\text{count}]Tr[mRNA]T[t] =$$

$$(k \text{ IF } V[\text{count}]G[A] > 0 \text{ AND } V[\text{count}]P[B] >$$

$$0 \text{ and } V[\text{count}]C[RNA] > 0 \text{ ELSE } 0) \bullet \Delta t -$$

$$c3 \bullet k2 \bullet V[\text{count}]Tr[mRNA] \bullet \Delta t + V[\ldots] \ldots - V[\ldots] \ldots$$

$$V[\text{count}]C[RNA]T[t+\Delta t] - V[\text{count}]C[RNA]T[t] =$$

$$c3 \bullet k2 \bullet V[\text{count}]Tr[mRNA] \bullet \Delta t - [k \text{ IF } V[\text{count}]G[A] >$$

$$0 \text{ AND } V[\text{count}]P[B] > 0 \text{ and } V[\text{count}]C[RNA] >$$

$$0 \text{ ELSE } 0) \bullet \Delta t + V[\ldots] \ldots - V[\ldots] \ldots$$

There are alternative implementations. For example, instead of the substitution made above, we can calculate kinetic laws separately and substitute the numeric values to specific reaction rates iteratively.

A benefit of such a structured pathway model, wherein the pathway elements are associated with interaction data, such as interaction type and/or stoichiometric coefficients and/or location, is that flux rate equations, such as the equations described above, can be generated by an automatic modelling process, which greatly facilitates computer-aided simulation of biochemical pathways. Because each kinetic law has a database relation to an interaction and each interaction relates, via a specific connection, to a biochemical entity, the modelling process can automatically combine all kinetic laws that describe the creation or consumption of a specific biochemical entity and thereby automatically generate flux-balance equations according to the above-described examples.

Another benefit of such a structured pathway model is that hierarchical pathways can be interpreted by computers. For instance, the user interface logic may be able to provide easily understandable visualizations of the hierarchical pathways as will be shown in connection with FIG. 8.

FIG. 8 shows a visualized form of a pathway, generally denoted by reference numeral 800. A user interface logic draws the visualized pathway 800 based on the elements 212 to 224 shown in FIGS. 1 and 7A. Circles 810 represent biochemical entities. Boxes 820 represent interactions and edges 830 represent connections. Solid arrows 840 from a biochemical entity to an interaction represent substrate connections where the biochemical entity is consumed by the interaction. Solid arrows 850 from an interaction to a biochemical entity represent product connection where the biochemical entity is produced by the interaction. Dashed arrows 860 represent activations where the biochemical entity is neither consumed nor produced but it enables or accelerates the interaction. Dashed lines with bar terminals 870 represent inhibitions where the biochemical entity is neither consumed nor produced but it inhibits or slows down the interaction. The non-zero stoichiometric coefficients are associated with the substrate or product connections 840, 850. In control connections (eg activation 860 or inhibition 870) the stoichiometric coefficients are zero.

Also, measured or controlled variables can be visualized and localized on relevant biochemical entities. For example, reference numeral 881 denotes the concentration of a biochemical entity, reference numeral 882 denotes the reaction rate of an interaction and reference numeral 883 denotes the flux of a connection.

The precise roles of connections, kinetic laws associated with interactions and the biologically relevant location of each pathway provide improvements over prior art pathway models. For instance, a model as shown in FIGS. 7A to 8 supports descriptions of varying detail levels by varying the number of elements. Further, the model supports the inclusion of explicit kinetic laws if they are known.

This technique supports graphical representations of measurement results on displayed pathways as well. The measured variables can be correlated to the details of a graphical pathway representation based on the names of the objects.

Note that the data base structure denoted by reference numerals 200 and 700 (FIGS. 2 and 7A) provide a means for storing the topology of a biochemical pathway but not its visualization 800. The visualization can be generated from the topology, and stored later, as follows. The elements and interconnections of the visualization 800 are directly based in the stored pathways 700. The locations of the displayed elements can be initially selected by a software routine that optimizes some predetermined criterion, such as the number of overlapping connections. Such techniques are known from the field of printed-circuit design. The IMS may provide the user with graphical tools for manually cleaning up the visualization. The placement of each element in the manually-edited version may then be stored in a separate data structure, such as a file.

Experiments

The IMS preferably comprises an experiment project manager. A project comprises one or more experiments, such as sampling, treatment, perturbation, feeding, cultivation, manipulation, purification, cloning or other combining, separation, measurement, classification, documentation, or in-silico workflows.

A benefit of an experiment project manager is that all the measurement results or controlled conditions or perturbations ("what"), biomaterials and locations in biomaterials ("where") and timing of relevant experiments ("when") and methods ("how") can be registered for the interpretation of the experiment data. Another benefit comes from the possibility to utilize the variable description language when storing experiment data as data sets explained earlier.

FIG. 9A shows an experiment object in an experiments section of the IMS. As stored in the IMS, each project 902 comprises one or more experiments 904. Each experiment 904 has relations to equipment data 906, user data 908 and method data 910. Each method entity 910 relates to experiment input 914 and experiment output 920. The experiment input 914 connects relevant input, such as a biomaterial 916 (eg population, individual, reagent or sample) or a data entity 918 (eg controlled conditions) to the experiment, along with relevant time information.

The experiment output 920 connects relevant output, such as a biomaterial 922 (eg population, individual, reagent or sample) or a data entity 924 (eg measurement results, documents, classification results or other results) to the experiment, along with relevant time information. For instance, if the input comprises a specific sample of a biomaterial, the experiment may produce a differently-numbered sample of the same organism. In addition, the experiment output 920 may comprise results in the form of various data entities (such as the data sets shown in FIGS. 6A and 6B, or documents or spreadsheet files). The experiment output 920 may also comprise a phenotype classification and/or a genotype classification in data entities.

Data traceability will be improved by the fact that the experiment input 914 and experiment output 920 have a relevant time, as denoted by items 915 and 921 respectively. The times 915, 921 indicate times when the relevant biochemical event, such as sample taking, perturbation, or the like, took place. Data traceability will be further described in connection with FIGS. 11A and 11B.

An experiment has also a target 930, which is typically a biomaterial 932 (eg population, individual, reagent or sample) but the target of in-silico experiments may be a data entity 934.

The method entity 910 has a relation to a method description 912 that describes the method. The loop next to the method description 912 means that a method description may refer to other method descriptions.

The experiment input 914 and experiment output 920 are either specific biomaterials 916, 922 or data entities 918, 924, which are the same data elements as the corresponding elements in FIG. 2. If the experiment is a wet-lab experiment, the input and output biomaterials 916, 922 are two instances (same or different) of biomaterial 210 in FIG. 2. For example, they may be two specific samples 210-4.

Because the biochemical information (reference numeral 200 in FIG. 2) and the project information are described with common data entities, the project manager is able to track the history of each piece of information. It is also able to monitor productivity as an amount of added information per resource (such as person year).

The experiment project manager preferably comprises a project editor having a user interface that supports project management functionality for project activities. That gives all the benefits of standard project management that are useful in systems biochemical projects as well.

A preferred implementation of the project editor is able to trace all biomaterials, their samples and all the data through the various experiments including wet-lab operations and in-silico data processing.

An experiment project can be represented as a network of experiment activities, target biomaterials and input or output deliverables that are biomaterials or data entities.

In terms of complexity, FIG. 9A shows a worst-case scenario. Few, if any, real-life experiments comprise all the elements shown in FIG. 9A. For instance, if the experiment is a medical or biochemical treatment, the input and output sections 914, 920, typically indicate a certain patient or a biochemical sample. An optional condition element may describe the condition of the patient or sample before treatment. The output section is a treated patient or sample.

In case of sampling the input section indicates a biomaterial to be sampled, and the output section indicates a specific sample. In case of sample manipulation the input section indicates a sample to be manipulated and the output section indicates the manipulated sample. In a combination experiment the input section indicates several samples to be combined and the output section indicates the combined, identified sample. Conversely, in a separation experiment the input section indicates a sample to be separated and the output section indicates several separated, identified samples. In a measurement experiment the input section indicates a sample to be measured and the output section is a data entity containing the measurement results. In a classification experiment the input section indicates a sample to be classified and the output section indicates a phenotype and/or genotype. In a cultivation experiment the input and output sections indicate a specific population, and the equipment section may comprise identities of the cultivation vessels.

In order to describe complex experiments, there may be experiment binders (not shown separately) that combine several experiments in a manner which is somewhat analogous to the way the pathway connections 700, 720, 730 combine various pathways.

Figure 9B:
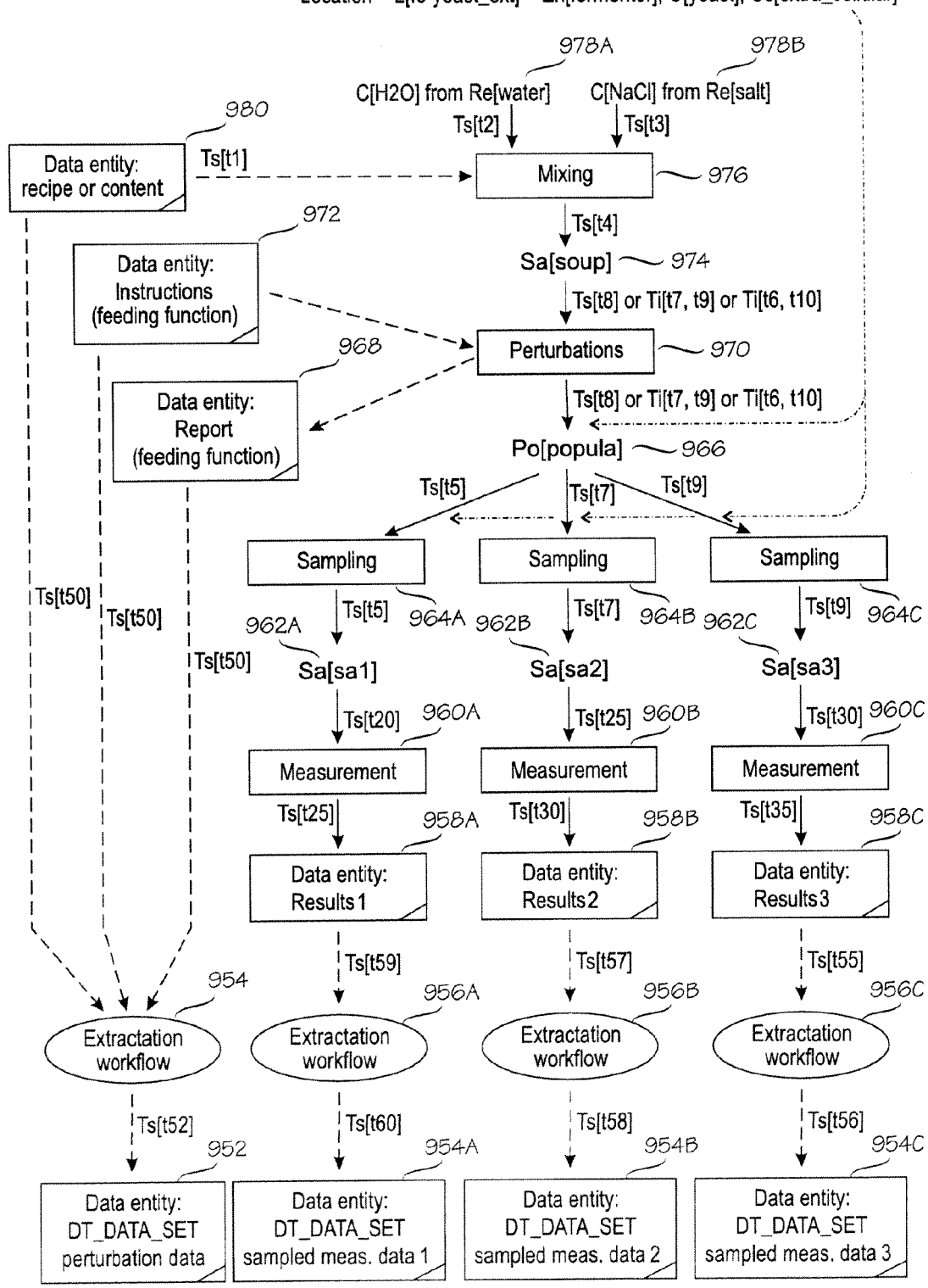
FIG. 9B illustrates creation of a project plan from a set of desired results.

FIG. 9B illustrates creation of a project plan from a set of desired results. The project plan shown in FIG. 9B is a representative sample of project plans that can be created with the system shown in FIG. 9A. As shown in FIG. 9A, an experiment input 914 is processed by a method 910 to an experiment output 920, which may be applied as experiment input to another method, and so on. In FIG. 9B, rectangles like mixing 976 and perturbations 970 represent methods, while biomaterials, such as sample 974 and population 966, represent experiment input and/or output.

If the project plan shown in FIG. 9B is created on a graphical user interface by a designer, it is self-explanatory. But what makes it interesting is that the systematic project structure shown in FIG. 9A makes it possible to provide the IMS with a routine for automatically creating a project plan, or at least some of its intermediate acts, from a set of desired results.

Assume that a researcher wishes to obtain four data sets, namely perturbation data 952 that describes a set or perturbations to be entered into a population 966 and sampled measurement data 954A-954C from the population 966. The population 966, labelled Po[popula] and specified in the data sets 952 and 954A-954C, is an instance of a biomaterial experiment target 932 and 930 (see FIG. 9A). It will be affected by perturbations 970 at times specified in data set 952. The perturbation 970 is prepared by a mixing experiment 976 derived from perturbation variable data of the data set 952 and a method description 912 of the mixing method 910, with a recipe data entity 980 as experiment input 918 and biomaterials 978A and 978B as experiment input 916 and a sample 974 as a biomaterial experiment output 922. Three sampling operations 964A-964C will create three samples 962A-962C of the experiment target 966, ie Po[popula], at times specified in the data sets 954A-954C. The samples 962A-962C are analyzed in measurement experiments 960A-960C derived from measurement variable data of data sets 954A-954C and method descriptions 912 of the measurement methods 910. The samples 962A-962C are instances of experiment inputs 916 (see FIG. 9A) and the data entities 958A-958C are instances of experiment outputs 924.

In this way, experiment targets 930 and intermediate experiments 904 and their inputs 914 and outputs 920 with required timing 915 and 921 can be determined by the information of data sets 952 and 954A-954C and predefined methods 910 and method descriptions 912 when variable data of data sets are mapped into methods in method descriptions 912.

The problem faced by the logic for creating automatic project plans is how to determine the intermediate steps from data sets 954A-954C to the population 966. The logic is based on the idea that in a typical research facility, any type of measurement data can only be created by a limited set of measurement methods. Assume that the first data set 954A contains data for which there is only one method description 912 (see FIG. 9A). In such a case that method, ie measurement 960A, can be selected automatically. If the remaining data sets 954B and 954C contain types of data that can be obtained by several measurement methods, the logic can offer the potential method candidates for selection by the user. But as soon as the user has selected appropriate measurement methods 960B and 960C, the logic can infer that three samples 960A to 960C are needed for the three measurements. Since three samples are needed, three sampling operations 964A to 964C of the population 966 are needed as well, since sampling is the only operation that produces a sample. The same idea can be applied to derive specific mixing or other preparation experiments for perturbation experiments targeted for the research target. Thus the systematic object-based project description shown in FIG. 9A can be used by a logic for automatically creating at least some intermediate acts in a project plan as shown in FIG. 9B.

Furthermore, the logic can also infer advantageous time stamps for the acts of the project plan. As shown in FIG. 9B, each act has an associated time stamp Ts[time]. Assume that the researches wishes to determine beforehand an optimized set of time stamps for the sampling of population 966. The time stamps are shown as Ts[t5], Ts[t7] and Ts[t9]. The logic can use the kinetic laws described in connection with the pathways (FIGS. 7A to 8) and carry out a simulation of what will happen in the population 966 in response to the perturbations 970. Most likely the simulation will result in an activity that takes some time to start, then peaks and finally levels off. The researcher or the logic itself can determine an optimized set of time stamps such that all the major phases (start, peak, level-off) of the activity will be adequately covered by measurements.

Biomaterial Descriptions

FIG. 10 shows an example of an object-based implementation of the biomaterials section of the IMS. Note that this is but one example, and many biomaterials can be adequately described without all elements shown in FIG. 10. The biomaterial section 210, along with its sub-elements 210-1 to 210-4, and the location section 214 with its sub-elements 214-1 to 214-5 have been briefly described in connection with FIG. 2. In addition to the previously-described elements, FIG. 10 shows that a biomaterial 210 may have a many-to-many relation to a condition element 1002, a phenotype element 1004 and to a data entity element 1006. An optional organism binder 1008 can be used to combine (mix) different organism. For example, the organism binder 1008 may indicate that a certain population comprises x percent of organism 1 and y percent of organism 2.

A loop 1010 under the organism element 214-1 means that the organism is preferably described in a taxonomical description. The bottom half of FIG. 10 shows two examples of such taxonomical descriptions. Example 1010A is a taxonomical description of a specific sample of coli bacteria. Example 1010B is a taxonomical description of white clover.

The variable description language described in connection with FIGS. 3A to 3C can be used to describe variables relating to such biomaterials and/or their locations. Example:

$$V[concentration]P[P53]U[mol/l]Id[Patient\ X]L[human\ cytoplasm]=0.01.$$

A benefit of this kind of location information is an improved and systematic way to compare locations of samples and locations of theoretical constructs like pathways that need to be verified by relevant measurement results.

Another advantage gained by storing the biomaterials section substantially as shown in FIG. 10 relates to visualization of data. For example, biomaterials can be replaced with their phenotypes. An example of such replacement is that certain individuals are classified as "allergic", which is far more intuitive to humans than a mere identification.

Data Traceability

Figure 11A:
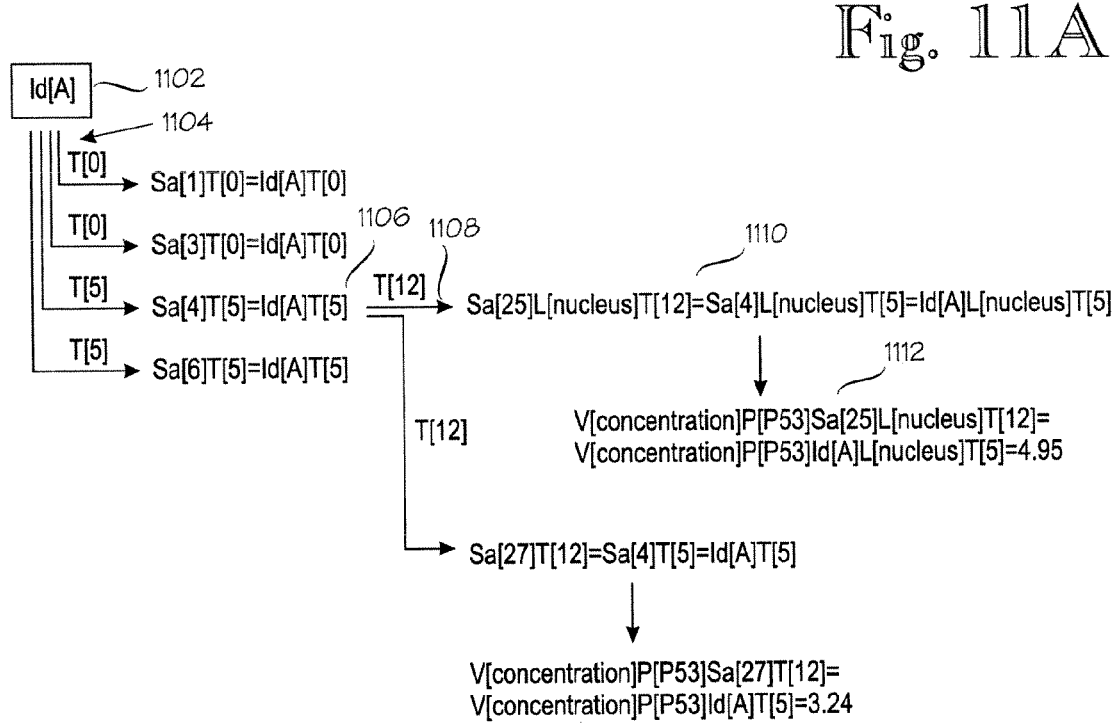
FIGS. 11A and 11B demonstrate data traceability in the light of two examples.
Figure 11B:
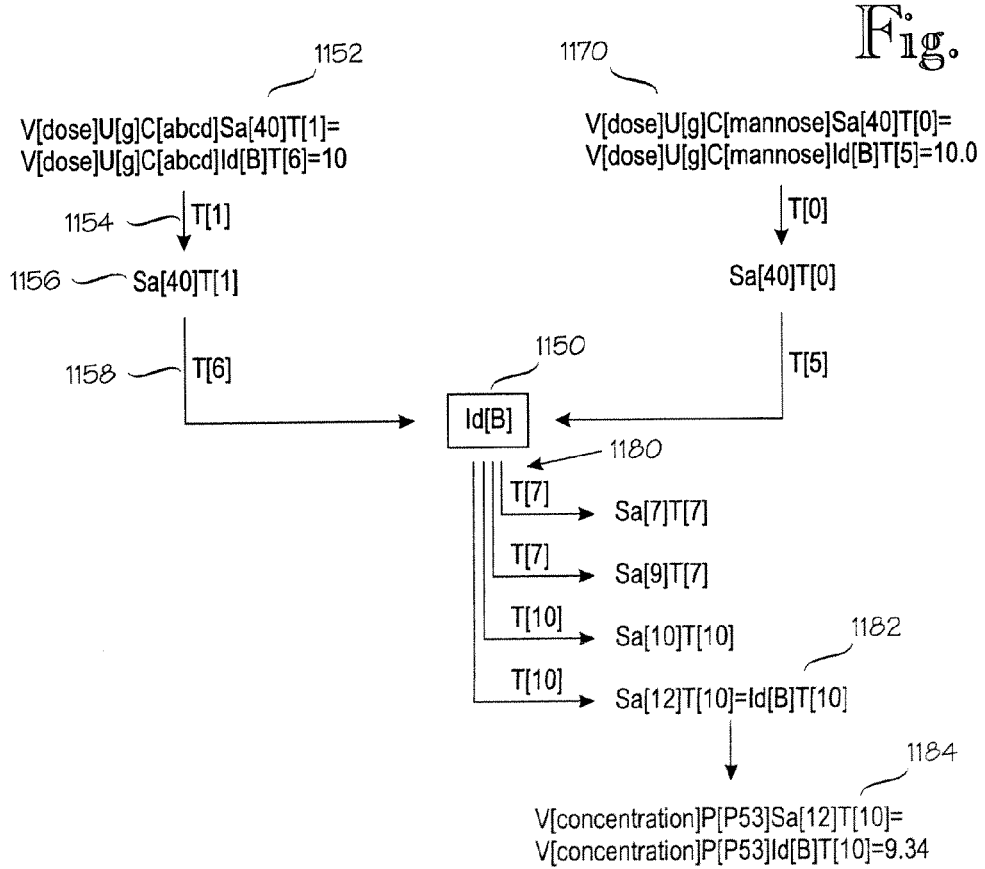

Data traceability is based on the time information 915 and 921 associated with experiment inputs and outputs 914 and 921, respectively (see FIG. 9A). FIGS. 11A and 11B demonstrate data traceability in the light of two examples. FIG. 11A shows a sampling scenario. All samples are obtained from a certain individual A, denoted by reference number 1102. Reference number 1104 generally denotes four arrows each of which corresponds to a certain sampling at a certain time. For example, at time 5 a sample 4 is obtained, as indicated by reference numeral 1106. Using the VDL shown in connection with FIGS. 3A to 4, sample 4 at time 5 can be expressed as Sa[4]T[5]. The expression Sa[4]T[5]=Id[A]T[5] means that sample 4 was obtained from individual A at time 5.

At time 12 two further samples are obtained from sample 4. As shown by arrow 1108, sample 25 is obtained from sample 4 by separating the nuclei. Reference numeral 1112 denotes an observation (measurement) of sample 25, namely the concentration of protein P53, which in this example is shown as 4.95.

FIG. 11B illustrates data traceability in a scenario in which a perturbation is caused by administering certain compounds to an individual B, 1150. As shown by reference numerals 1152 to 1158, a 10-gram dose of compound abcd is applied to sample 40 at time 1, and that sample is administered to individual B at time 6. Reference numeral 1160 denotes administration of mannose to individual B at time 5. The bottom half of FIG. 11B is analogous to FIG. 11A, and a separate description is omitted.

Showing images such as those contained in FIGS. 11A and 11B helps users to understand what the observations are based on. Benefits of improved data traceability include better understanding of relevant timing of experiments inputs and outputs as well as reduction of errors and easier explanation of anomalies.

It should be understood that real-life cases can be far more complex than what can reasonably be shown on one drawing page. Thus FIGS. 11A and 11B show the principle of data traceability. In order to support complex cases, the visualization logic should be preceded by user-activated filters that let users see only the topics of interest. For example, if a user is only interested in sample 25 shown in FIG. 11A, only the chain of events (samples) 1102-1106-1110-1112 can be displayed.

Workflow Descriptions

Figure 12A:
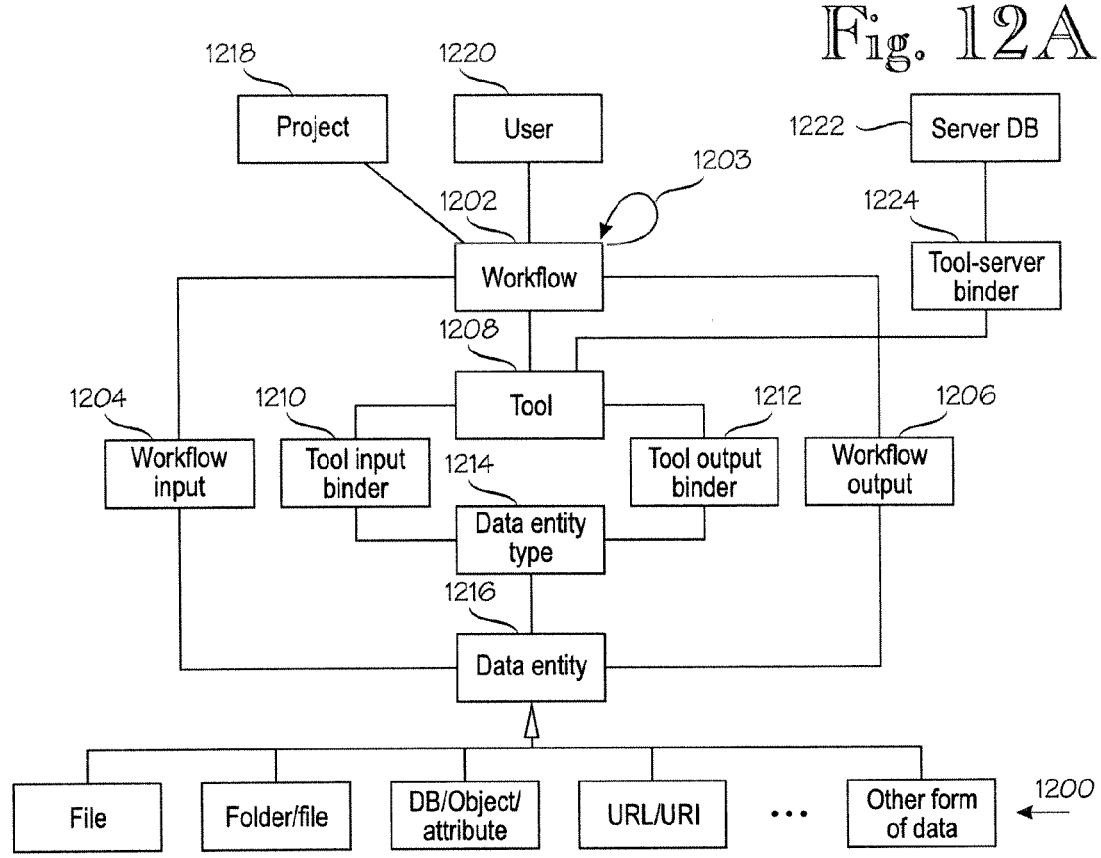
FIG. 12A shows an information-entity relationship for describing and managing complex workflows within the IMS.

FIG. 12A shows an information-entity relationship for describing and managing workflows of virtually arbitrary complexity within the IMS. A workflow 1202 may contain other workflows, as indicated by arrow 1203. The lowest level workflow contains a tool definition 1208. Each workflow has an owner user 1220. Each workflow belongs to a project 1218. (Projects were discussed in connection with FIGS. 9A and 9B.)

Tools are defined in terms of tool name, category, description, source, pre-tag, executable, inputs, outputs and service object class (if not the default). This information is stored in a tool table or database 1208.

Figure 16A:
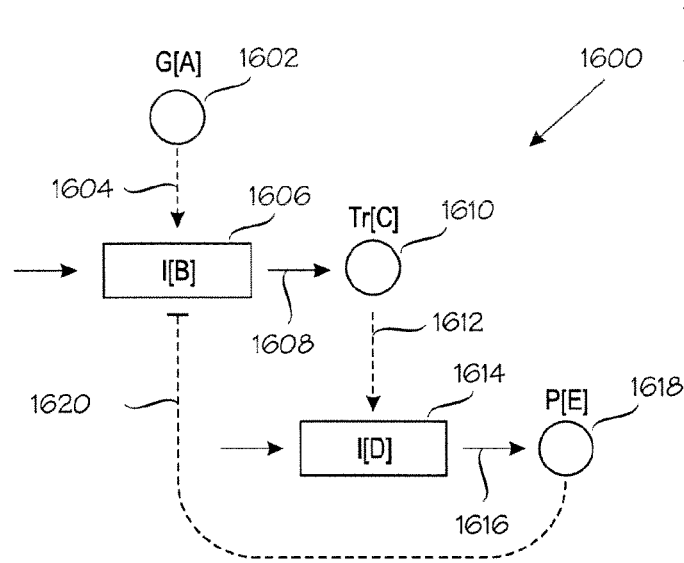
Figure 16B:
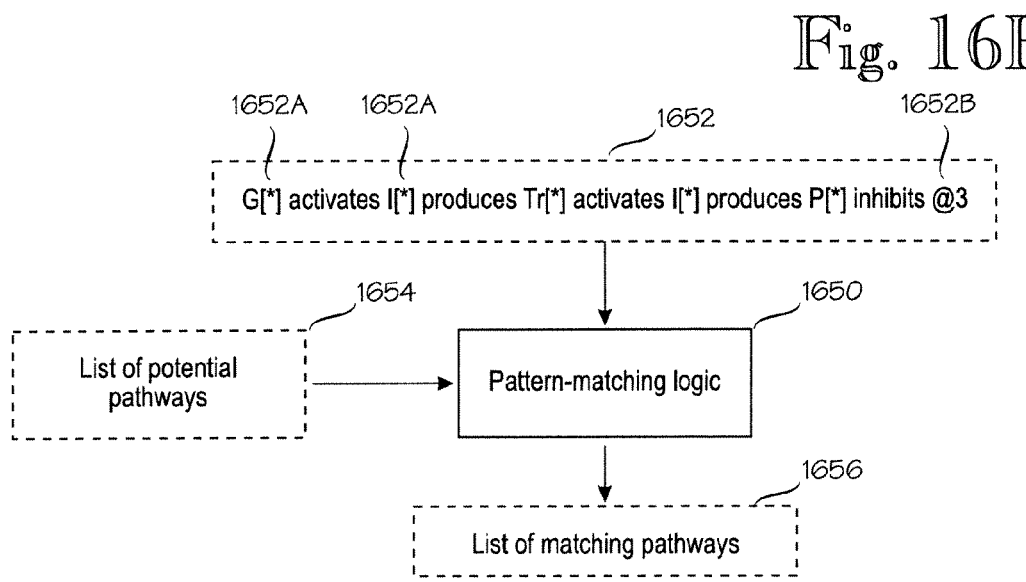

An input definition includes pre-tag, id number, name, description, data entity type, post-tag, command line order, optional-status (mandatory or optional). This information is stored into the tool input binder 1210 or tool output binder 1212. In a real-life implementation, it is convenient to store the tool 1208, the tool input binder 1210 and tool output binder 1212 in a single disk file, an example of which is shown in FIGS. 16A and 16B.

The data entity types are defined to the system in terms of data entity type name, description, data category (eg file, directory with subdirectories and files, data set, database, etc). There are several data entity types that belong to the same category but having different syntax or semantics and consequently belong to different data entity type for compatibility rules of existing tools. This information is stored in data entity type 1214. Tool server binder 1224 indicates a tool server 1222 in which the tool can be executed. If there is only one tool server 1222, the tool server binder 1224 can be omitted.

Typed data entities are used to control the compatibility of different tools that might be or might not be compatible. This gives the possibility to develop a user interface in which the systems assists users to create meaningful workflows without prior knowledge about the details of each tool.

The data entity instances containing user data are stored in data entity 1216. When workflows are built the relevant data entities are connected to relevant tool inputs through workflow inputs 1204 or workflow outputs 1206. Reference numeral 1200 generally denotes the various data entities, which in real-life situations constitute actual instances of input or output data.

Figure 12B:
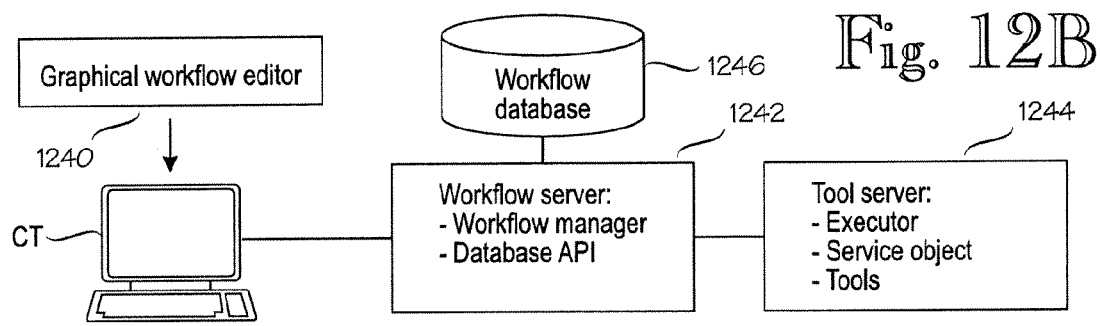
FIG. 12B shows a client-server architecture comprising a graphical workflow editor being executed in a client terminal.

FIG. 12B shows a client-server architecture comprising a graphical workflow editor 1240 being executed in a client terminal CT. The graphical workflow editor 1240 connects via a workflow server 1242 to an executor and a service object in a tool server 1244. The graphical workflow editor 1240 is used to prepare, execute and monitor and view workflows and data entities communicating with a workflow database 1246. The workflow server 1242 takes care of executing workflows by using one or more tool servers 1244. The address of the relevant tool server can be found from the server table 1222 (FIG. 12A).

Each tool server 1244 comprises an executor and a service object that is able to call any standalone tool installed on the tool server. The executor manages executing all the relevant tools of a workflow with relevant data entities through a standardized service object. The service object provides a common interface for the executor to run any standalone software tool. Tool-specific information can be described in an XML file that is used to initialize metadata for each tool in the tool database (item 1208 in FIG. 12A). The service object receives the input and output data and by using the tool definition information, it can prepare the required command line for executing the tool.

A workflow/tool manager as shown in FIGS. 12A and 12B easily integrates legacy tools and third-party tools. Other benefits of the workflow/tool manager include complete documentation of workflows, easy reusability and automatic execution. For instance, the workflow/tool manager can hide the proprietary interfaces of third-party tools and substitute them with the common GUI of the IMS. Thus users can use the functions of a common graphical user interface to prepare, execute, monitor and view workflows and their data entities.

Note that FIG. 12A shows an information-entity relationship that shows the mutual relations between different types of entities, tools etc. FIG. 12A shows, for example, that a tool input binder 1210 defines a relation between an input of a tool 1208 and a data entity type 1214, which may or may not be the same type as the one that represents the tool's output as defined by the tool's output binder 1212.

Figure 12C:
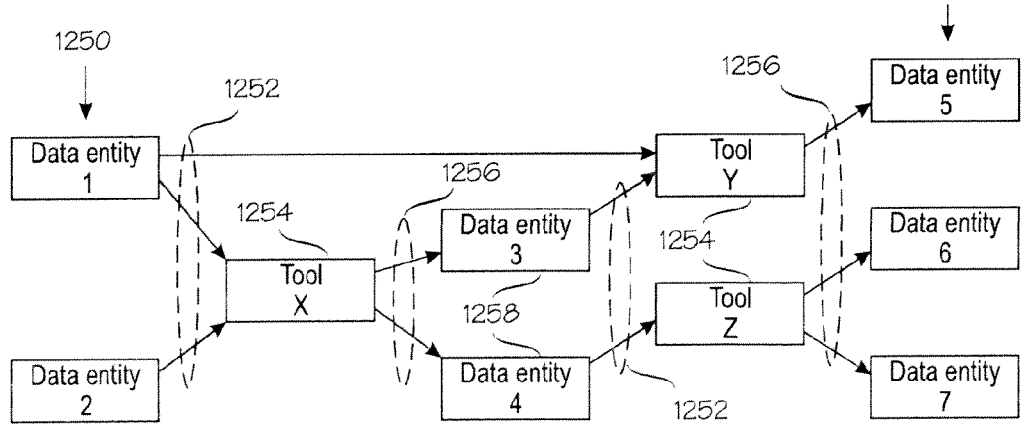
FIG. 12C shows how the workflow editor can represent workflows as a network of tools and data entities, such that data entities are inputs or outputs of tools.

FIG. 12C shows the interrelation of tools and data entities from an end user's point of view. The available tools and data entities can be combined as logical networks (workflows) of arbitrary complexity, wherein one tool's output is connected to the next tool's input, and so on. Note that each tool needs to be defined only once. For each instantiated execution of a tool, there is a child workflow 1202 (or work 1202' in FIG. 12D) that can be created for each graphical "tool" icon. Reference numeral 1250 denotes input data entities, which in this example are data entities 1 and 2. Reference numerals 1252 denote workflow inputs. Reference numerals 1254 denote the tools X, Y and Z used in this workflow. In this example the workflow inputs 1252 bind data entities 1 and 2 to child workflows using tool X and Y, and data entities 1, 3 and 4 also to child workflows using tool Y and Z. Reference numerals 1256 denote workflow outputs, which in this example bind data entities 3 and 4 to child workflows using tool X and data entities 5, 6 and 7 to child workflows using tools Y and Z. Reference numerals 1258 denote intermediate data entities that constitute the output from a child workflow that calls tool X, providing inputs to another child workflow that calls tools Y and Z. Reference numeral 1260 denotes output data entities, which in this example are data entities 5, 6 and 7. Each workflow input 1252 or workflow output 1256 is an instance of the respective class 1204, 1206 shown in FIG. 12A. Tool input binders 1210 and output binders 1212 are used in a graphical user interface to assist users in building workflows, by connecting tools and data entities with correct data entity types for each input or output.

As shown in FIG. 12C, the workflow inputs 1252 or workflow outputs 1256 collectively define a data flow network from the input data entities 1250 to its output data entities 1260, such that each workflow input 1252 connects a specific data entity to an input of a tool 1254 and each workflow output 1256 connects the tool's output to a specific data entity, which may be an intermediate data entity 1258 or an output data entity 1260. The tools are executed on the basis of topological sorting of workflows. Such workflows are most useful for complex tasks that need to be repeated over and over again with different inputs.

The embodiment shown in FIG. 12C hides certain abstract concepts, such as child workflows, workflow inputs and outputs but shows more concrete things, such as data entities, tools, tool inputs and tool outputs.

Figure 12D:
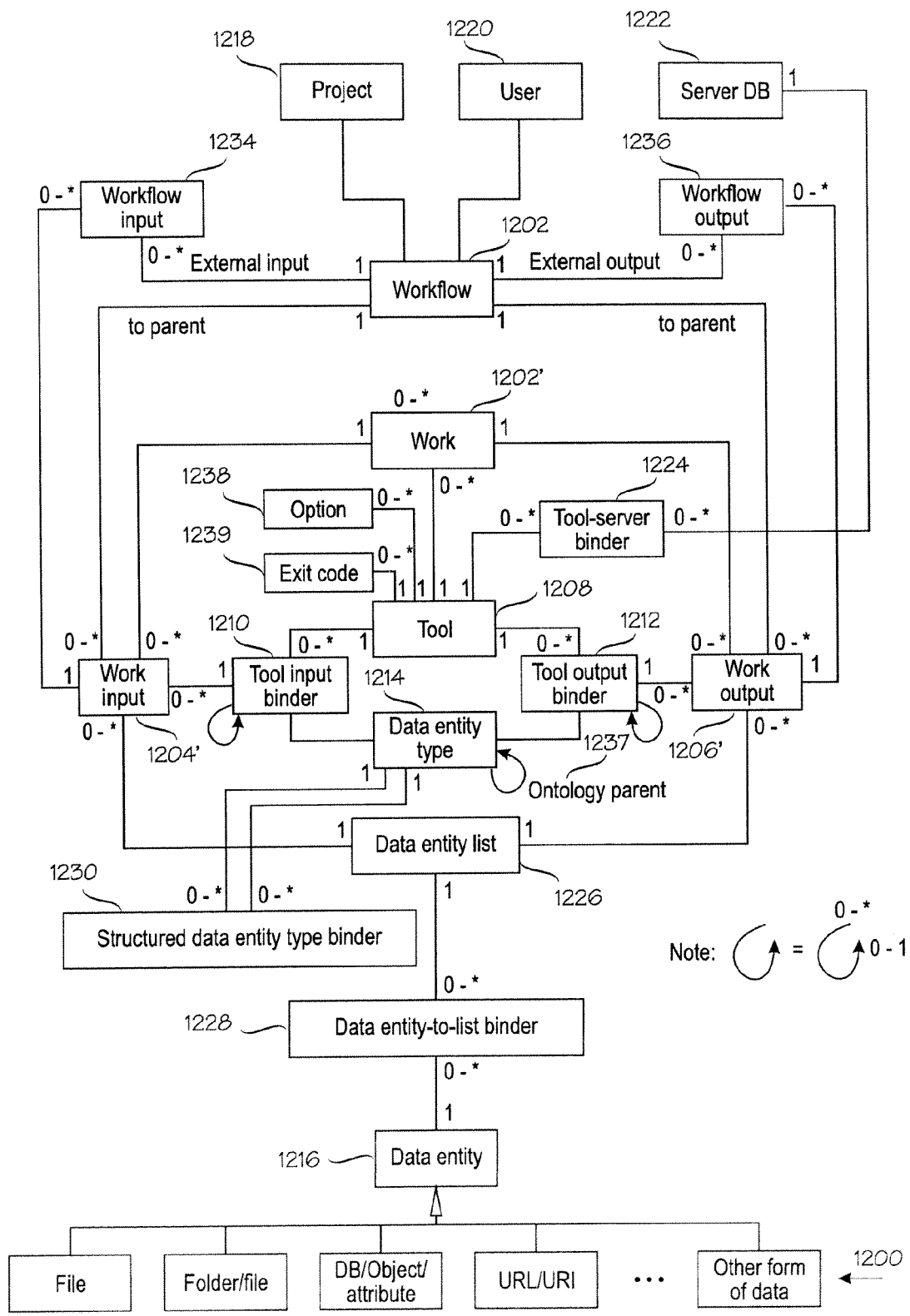
FIG. 12D shows an enhanced version of the information-entity relationship shown in FIG. 12A.

FIG. 12D shows an enhanced version of the information-entity relationship shown in FIG. 12A. Items with reference numerals lower than 1224 were described in connection with FIG. 12A and will not be described again. The embodiment shown in FIG. 12D has several enhancements over the one shown in FIG. 12A.

One enhancement consists of the fact that the hierarchical workflow 1202, 1203 of FIG. 12A has been divided into a workflow 1202 and work 1202', wherein the work 1202' is at the bottom level of the hierarchy and does not contain any child workflows. A workflow's external input and output are the workflow defined by workflow input 1236 and workflow output 1238, respectively. The external input and output of the workflow define the overall input and output, without any internal data entities that are used only within the workflow. The workflow's internal data entities are defined by work input 1204' and work output 1206'.

Another enhancement consists of the fact that the work input 1204' and work output 1206' are not connected to a data entity 1216 directly but via a data entity list 1226 which, in turn, is connected to the data entity 1216 via a data entity-to-list binder 1228. A benefit of this enhancement is that a work's input or output can comprise lists of data entities. This simplifies end-user actions when multiple data entities are to be processed similarly. Technically speaking, the data entity list 1226 specifies several data entities as an input 1204' or output 1206' of a work, such that each data entity in the list is processed by a tool 1208 separately but in a coordinated manner.

A third enhancement is a structured-data-entity-type binder 1230 for processing structured data entities, such as the data sets 610 and 620 shown in FIGS. 6A and 6B. Such data sets consist of four data entities (describing common, rows, columns and value matrix) each, and the structured data entities can be defined by the structured-data-entity-type binder 1230. Thus the end-users are not concerned with interrelations of the data entities.

Moreover, each tool 1208 may have associated options 1238 and/or exit codes 1239. The options 1238 may be used to enter various parameters to the software tools, as is well known in connection with script file processing. The options 1238 will be further discussed in connection with FIGS. 16B and 16B (see items 1650-1670 and 1696-1697). The exit codes (or error codes) 1239 can be used to convey the termination status of a tool back to a user via the service object, the executor, the workflow server and the graphical workflow editor. For instance, if the operation of a tool is interrupted because of some kind of processing error, there is little point in a subsequent tool to carry out its intended task but let the user know the termination status. Examples of exit codes will be shown in FIG. 16B (see section 1680).

Yet another optional enhancement shown in FIG. 12D is that the type definition 1214 contains an ontology definition. A benefit of the ontology definition is that the type checking of a tool to/from a data entity does not have to succeed literally but conceptually. For example, a tool's definition may specify that the tool outputs files in "Rich Text Format", while another tool's definition specifies that the tool processes (inputs) "text" files. A literal comparison of "text" and "Rich Text Format" will fail but an appropriately configured ontology definition is able to indicate that "Rich Text Format" is a subclass of "text" files, whereby the ontological type checking succeeds.

Figure 13:
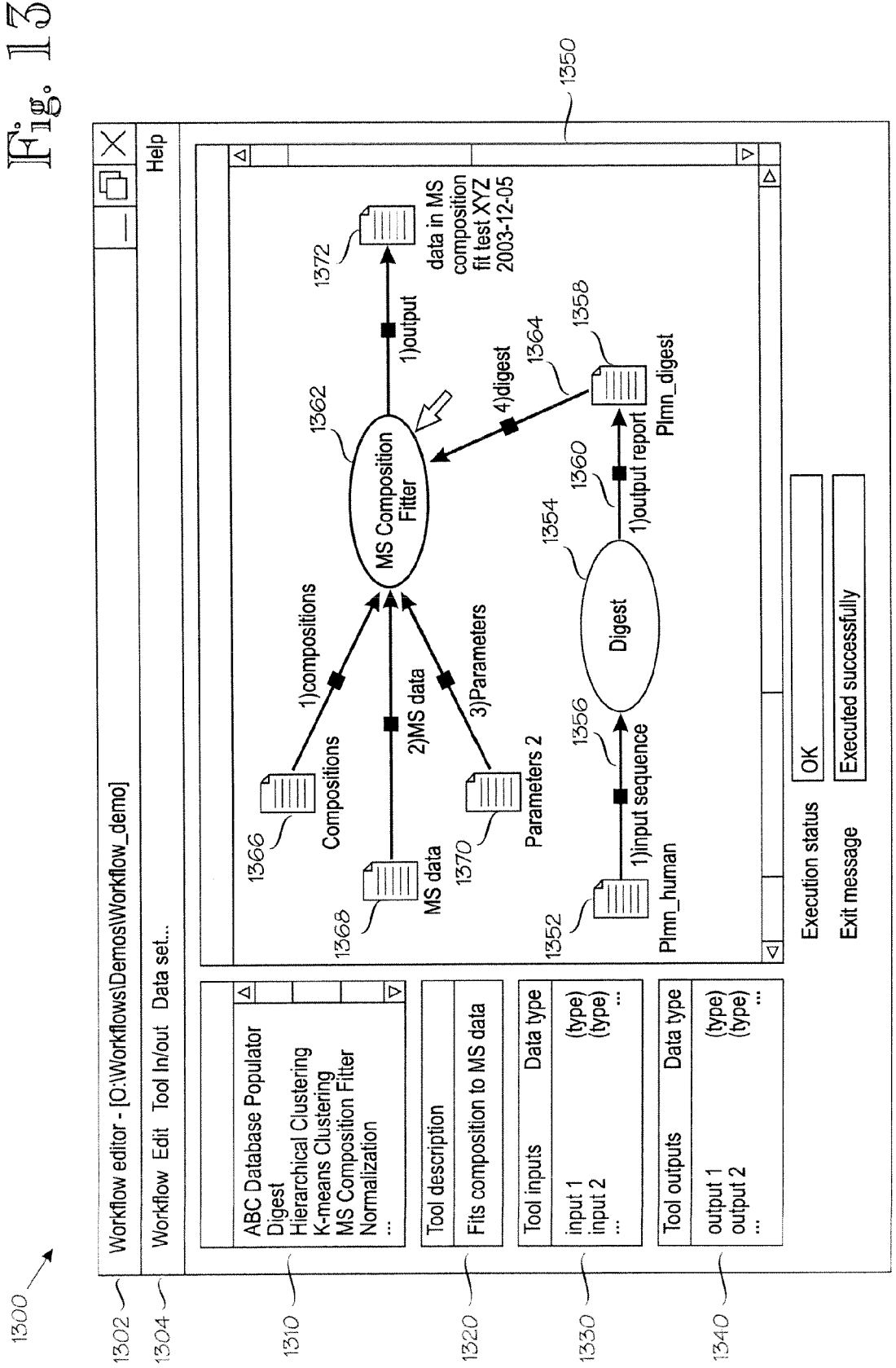
FIG. 13 shows an exemplary user interface for a workflow manager.

FIG. 13 shows an exemplary user interface 1300 for a workflow manager. A title bar 1302 and menu bar 1304 are self-evident to persons familiar with graphical user interfaces. A tool selector box 1310 lists all available tools. A tool descriptor box 1320 shows a description for the selected tool. A tool input box 1330 and tool output box 1340 list and describe, respectively, the selected tool's inputs and outputs. A graphical workflow editor box 1350 shows the contents of the workflow being edited, ie the interrelation of the various data entities and tools, in a graphical form. The graphical workflow editor box 1350 shows, in principle, similar subject matter as was shown in FIG. 12C, but in FIG. 12C the emphasis was on logical relations between tools, data entities and binders, while FIG. 13 shows a more realistic view of an actual user interface. In this example, data entity 1352 is an input of tool 1354, as shown by the connector arrow 1356. The output of tool 1354 is data entity 1358, as shown by connector arrow 1360. Data entity 1358, which is the output of tool 1354 will be used as one of the inputs of tool 1362, as shown by connector arrow 1364. Tool 1362 has three other inputs 1366, 1368 and 1370. In this example, inputs 1366 and 1368 are data entities, and input 1370 contains various optional or user-settable parameters. Another way of entering parameters, particularly non-optional parameters, will be shown in FIG. 16B (see option section 1650-1670 in configuration file 1600). The output of tool 1362 is data entity 1372, which is also the output of the entire workflow. Actually, the workflow being edited in the workflow editor box 1350 may be a child workflow of some parent or upper-level workflow, as shown by arrow 1203 in FIG. 12A, and the output of that child workflow will be used as an input in that upper-level workflow.

The elements in FIG. 13 relate to those in FIG. 12A or 12D as follows. Each data entity 1352, 1358, shown with a "file" type icon, such as icon 1352, is an instance of the data entity class 1216 in FIG. 12A or 12D. Tools shown in the tool selector box 1310 are instances of the tool class 1208 in FIG. 12A or 12D. They can be selected from the tool selector box 1310 when instantiating their potential executions as child workflows in FIG. 12A or works in FIG. 12D. Child workflows or works of relevant tools 1354 and 1362 are used in the workflow being edited as instances of child workflows 1202 in FIG. 12A or as instances of works 1202' in FIG. 12D.

The parent workflow being edited is an instance of workflow class 1202. The arrows 1356, 1364, etc., created by the graphical user interface in response to user input, represent instances of a work or workflow input 1204', 1204. These arrows connect a data entity as an input to a work that will be done by executing the tool when the workflow is executed. The relevant tool is indicated with a "tool" type icon, such as icon 1354. The tool input binders 1210 enable type checking of each connected instance of a data entity. The arrows 1360 represent instances of a work or workflow output 1206, 1206'. These arrows connect a data entity as an output from a work that will be done by executing the tool when the workflow is executed. The relevant tool is indicated with a "tool" type icon. The tool output binders 1212 enable type checking of each connected instance of a data entity.

A benefit of this implementation is that the well-defined type definition shown in FIGS. 12A and 12D supports thorough type-checking which ensures data reliability and integrity. In the user interface 1300, the type checking may be implemented such that an interactive connection between a data entity and a tool can only be performed if the type check is successful. In addition, the data entity types may be shown in the selected tool's input box 1330 and output box 1340.

Again, abstract concepts, such as child workflow and workflow input, workflow output, work input and work output are hidden from the users of the graphical user interface, but more concrete elements, such as data entities, tools, tool inputs and tool outputs are visualized to users as intuitive icons and arrows.

In case of quantitative data, the data entities 1216, 1352, etc. are preferably organized as data sets 610, 620, and more particularly as variable value matrixes 614, 624, that were described in connection with FIGS. 6A and 6B. A benefit of the variable value matrixes 614, 624 in this environment is that the software tools, which may be obtained from several sources, only have to process arrays but no dimensions or matrix row or column descriptors.

The graphical user interface preferably employs a technique known as "drag and drop", but in a novel way. In conventional graphical user interfaces, the drag and drop technique works such that if a user drags an icon of a disk file on top of a software tool's icon, the operating system interprets this user input as an instruction to open the specified disk file with the specified software tool. But the present invention preferably uses the drag and drop technique such that the specified disk file (or any other data entity) is not immediately processed by the specified tool. Instead, the interconnection of a data entity to a software tool is saved in the workflow being created or updated. Use of the familiar drag and drop metaphor to create saved workflows (instead of triggering ad-hoc actions) provides several benefits. For example, the saved workflows can be easily repeated, with or without modifications, instead of recreating each workflow entirely. Another benefit is that the saved workflows support tracing of workflows.

Dedicated tool input and output binders make it possible to use virtually any third-party data processing tools. The integration of new, legacy or third-party tools is made easy and systematic.

The systematic concept of workflows hides the proprietary interfaces of third-party tools and substitute the proprietary interfaces with a common graphical user interface of the IMS. Thus users can use the functions of a common graphical user interface to prepare, execute, monitor and view workflows and their data entities. In addition, such a systematic workflow concept supports systematic and complete documentation, easy reusability and automatic execution.

The concept of data entity provides a general possibility to experiment with any data. However, the concept of data entity type makes possible to understand, identify and control the compatibility of different tools. Organization of quantitative data as data sets, each of which comprises a dimensionless variable value matrix, provides maximal compatibility between the data sets and software tools from third parties, because the tools do not have to separate data from dimensions or data descriptors.

Because of the graphical interface, researchers with a biochemical expertise can easily connect the biologically relevant data entities to or from available inputs or outputs and get immediate visual feedback. Inexperienced users can reuse existing workflows to repeat standard workflows merely by changing the input data entities. The requirement to learn the of the syntactic and semantic details of each specific tool's command line can be delegated to technically-qualified persons who integrate new tools to the system. This benefit stems from the separation of the tool definitions from the workflow creation. Biochemical experts can concentrate on workflow creation (defined in terms of data entities, works, workflows, work inputs, workflow inputs, work outputs, workflow outputs), while the tool definitions (tools, tool input binders, tool output binders, options, exit codes), are delegated to Information-technology experts.

Automatic Population of Pathways from a Gene Sequence Database

An IMS having a pathway model substantially as described in connection with FIGS. 7A to 8 supports incomplete pathways. This is because the pathways are defined in terms of elementary components which can be added when more information is obtained. A benefit of this capability is that the IMS can be provided with hardware and software means for automatic population of pathways from external (often commercial) sequence databases. What is needed is access means to external databases, parsing logic for each specific database and a logic for deriving the pathway components (or at least some of them) from the feature tables or other information provided by the external databases. Note that the sequence databases provide no explicit information on pathway models. They merely provide information on genes, their coding areas and/or the proteins coded by the genes. But a suitable logic can infer at least some of the pathway components from this information. The logic can interpret annotations provided by the sequence databases as a huge mass of relations by means of well-defined biochemical entities (a specific gene and a specific set of proteins) as soon as these relations, of which the sequence databases tell explicitly nothing, have been stored in the pathway database (FIGS. 7A and 7B). Interactions (transcriptions and translations), of which the sequence databases also tell nothing, cannot be completely described using basic biochemical knowledge, but by means of well-defined biochemical entities and basic biochemical concepts, the connections between interactions can be completely described in the pathway model. It is not even necessary for the sequence database to contain information on transcripts. Instead, the inventive logic can determine the transcripts, identify and name them. Naming is often necessary because mRNA molecules are usually not named similarly to genes or proteins.

Thus an IMS with a pathway model as described above, primarily in connection with FIGS. 7A to 8, is based on connections and interactions and the IMS supports incomplete pathway models. It is a useful addition to determine the connections automatically from external databases, even if the interactions have to be completed afterwards when more information is available.

As used herein, biology's central dogma means current scientific view of microbiological processes, and more particularly, transcription of specific genes into specific transcripts and translation of specific transcripts into specific proteins. But systematic pathways with detailed biological central dogma information simply do not exist. Such pathways would be a reasonable starting point when building a realistic gene regulation network based on genes, transcripts and proteins. Prior art pathways only contain partial information (such as genes connected together if a product of one gene is a known regulator of another gene). Relationships of genes, transcripts and proteins are not largely described in machine-readable pathways. One explanation is that transcripts are not systematically identified and, consequently, they are not easily presented as elements of interactions in pathways. Creation of large pathways is also hampered by several problems, such as naming and modelling pathways scalability, etc. Pathways according to the central dogma tend to be complex, and it is far from trivial to realize that pathways of such complexity can be adequately modelled at all.

This embodiment takes well-identified genes from any typical DNA sequence database that contains identified genes with their DNA sequences. This input data does not include explicit pathway data, such as interactions, which may explain why the potential of the hidden pathway information in the DNA sequence database has been ignored so far. A typical DNA sequence database provides annotations of coding areas of each gene that provides a specific part of DNA sequence known to code a part of a transcript and/or part of a protein. Some DNA sequence databases are available in specific flat file formats or in XML formant, containing so-called feature tables or FT lines for specific keyword annotations (eg "CDS" for coding area/sequence) and a field that indicates sequential location of the annotated feature. Typically there are database references for genes and sometimes for proteins as well.

A gene can be identified objectively by its DNA sequence and its place on a chromosome and other genomic molecule carrying genes and subjectively by various names and database references.

A transcript can be identified objectively by its RNA sequence that is derived from the DNA sequence of the relevant gene. Messenger RNAs contain the RNA sequence that has been derived from the protein coding areas of the DNA sequence of the relevant gene. Each relevant transcript needs to be named. It can be named by the relevant gene if there is no other gene products otherwise it can be named by the gene and the protein it codes.

Three consecutive bases of a RNA sequence code one amino acid for the sequence of a protein. This means that one messenger RNA codes one protein that can be identified objectively by its amino acid sequence or subjectively by its several names or database references. The similarity of biochemical entities needs to be checked based on objective identification data. The names of biochemical entities must be used consistently in all applications that process the pathways.

This embodiment combines a pathway model, a logic for modifying and checking network topology of pathways and a management of objective and subjective identifications of biochemical entities (at least for genes, transcripts and proteins) based on gene sequence data, database reference data structure having the consistently used name of a biochemical entity associated with database name, id_name used in the database and id_string containing a subjective identification of the biochemical entity. The sequence data and subjective identifications are taken from a gene sequence databases that has no explicit interaction or pathway data.

Figure 14A:
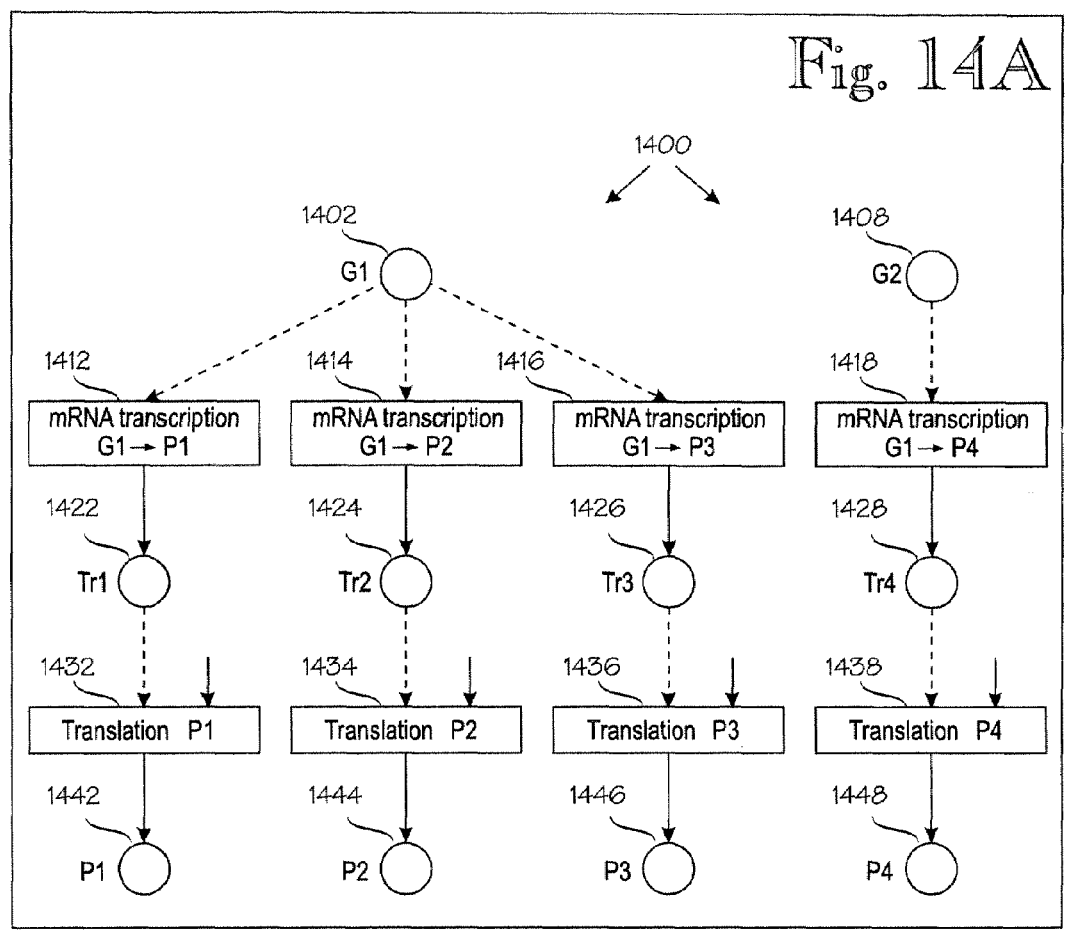
FIG. 14A to 14C illustrate a process for automatic population of pathways from a gene sequence database.

FIG. 14A illustrates a process 1400 for automatic population of pathways from a gene sequence database. In this example, there are two identified genes G1 and G2, denoted by reference numerals 1402 and 1408, in a sequence database. There are annotated DNA sequences in the feature table of the database.

In typical gene sequence databases, there are line identifiers, keywords, and sequential location or qualifier information for feature annotations. Although there are many different identifiers, keywords and qualifiers, it is possible to utilize some general commonalities.

For example, EMBL sequence database has feature tables as follows:

| Line | Key | Location/Qualifier |
| --- | --- | --- |
| FT | CDS | 22..2892 |
| FT | ... | |
| FT | | db_xref="SWISS-PROT:P49746" |
| FT | ... | |
| FT | | /gene="THBS3" |
| FT | ... | ... |

There are FT lines (feature table) having CDS (coding sequence) keywords indicating coding area and specific qualifiers that provide various database references to genes (/gene="THBS3") and their proteins (db_xref="SWISS-PROT:P49746"). This means that the gene identified by THBS3 has a protein product identified by "SWISS-PROT: P49746" and there must be an mRNA between the gene and the protein. Names need to be converted to the recommended names (see the name tables 226 in FIG. 2).

Let us assume that there are features annotated to have gene G1 (denoted by reference numeral 1402) with splice variant products P1, P2 and P3 (reference numerals 1442, 1444 and 1446). In such a case, an automatic population routine can infer that there must be three splice variant mRNAs, namely Tr1=mRNA from G1 to P1, Tr2=mRNA from G1 to P2, and Tr3=mRNA from G1 to P3. These splice variant mRNAs are denoted by reference numerals 1422, 1424 and 1426.

Let us further assume that there is a feature annotated to have gene G2, 1408 with one product P4, 1448. Then the automatic population routine can infer that there must be one mRNA, namely Tr4=mRNA, 1428, from G2 to P4.

Based on the above information, a skeleton pathway such as the one shown in FIG. 14A, can be created automatically.

Initially, the transcription interactions can be mechanically completed with ribonucleotide substrates, and afterwards with known transcription factors. The translation interaction can be completed with amino acids and ribosome. The interactions are not yet complete but RNA sequence databases can be used to form translation interactions if there are annotated features with an identified mRNA and a protein.

In terms of hardware and software, the IMS needs an access to external databases. Many databases can be accessed with an ordinary Internet browser. Accordingly, the automatic population software needs to emulate an Internet browser or otherwise output compatible commands. In addition, the IMS needs a parsing logic and information on how the output of each database is arranged.

Figure 14B:
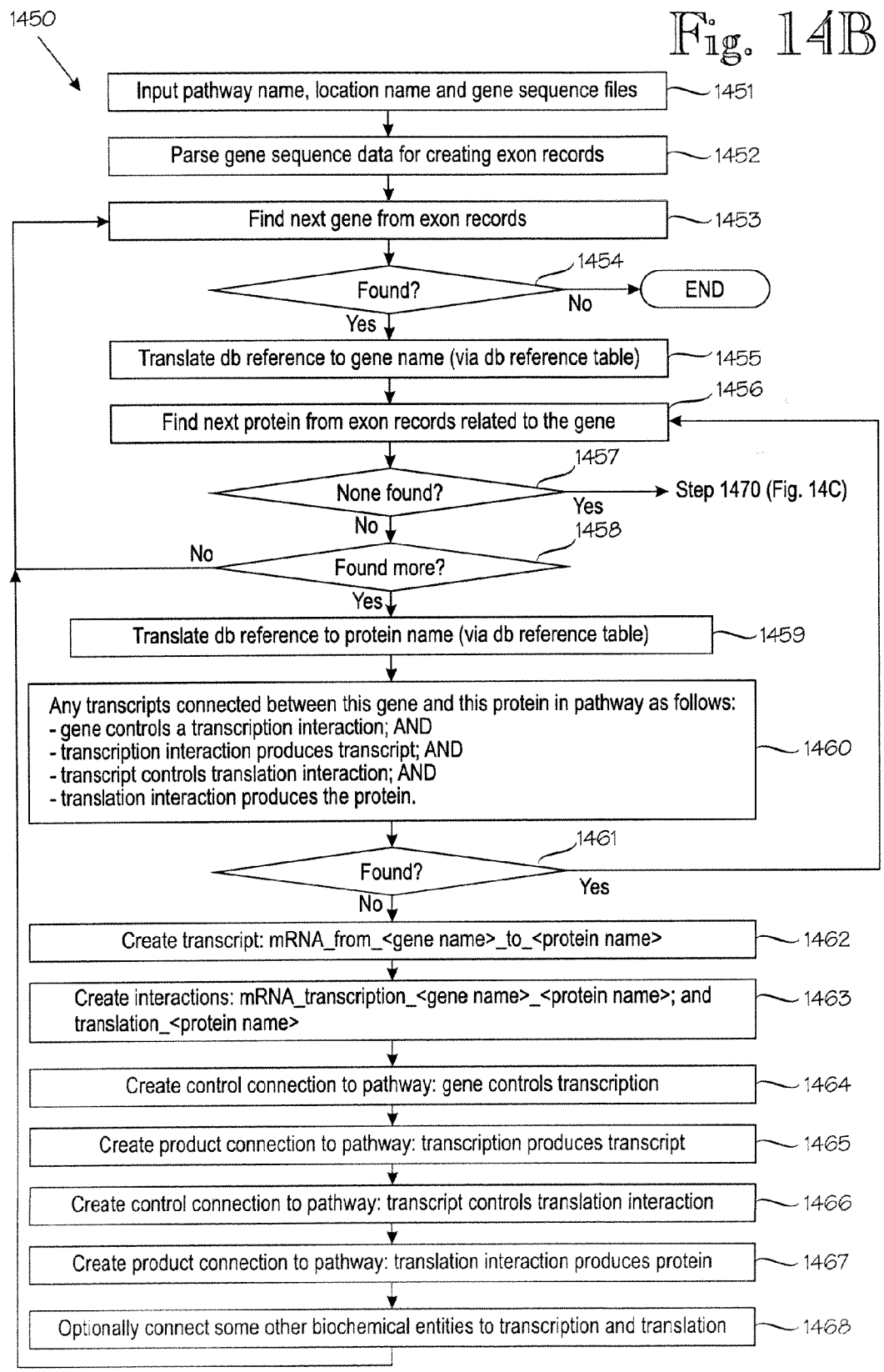
Figure 14C:
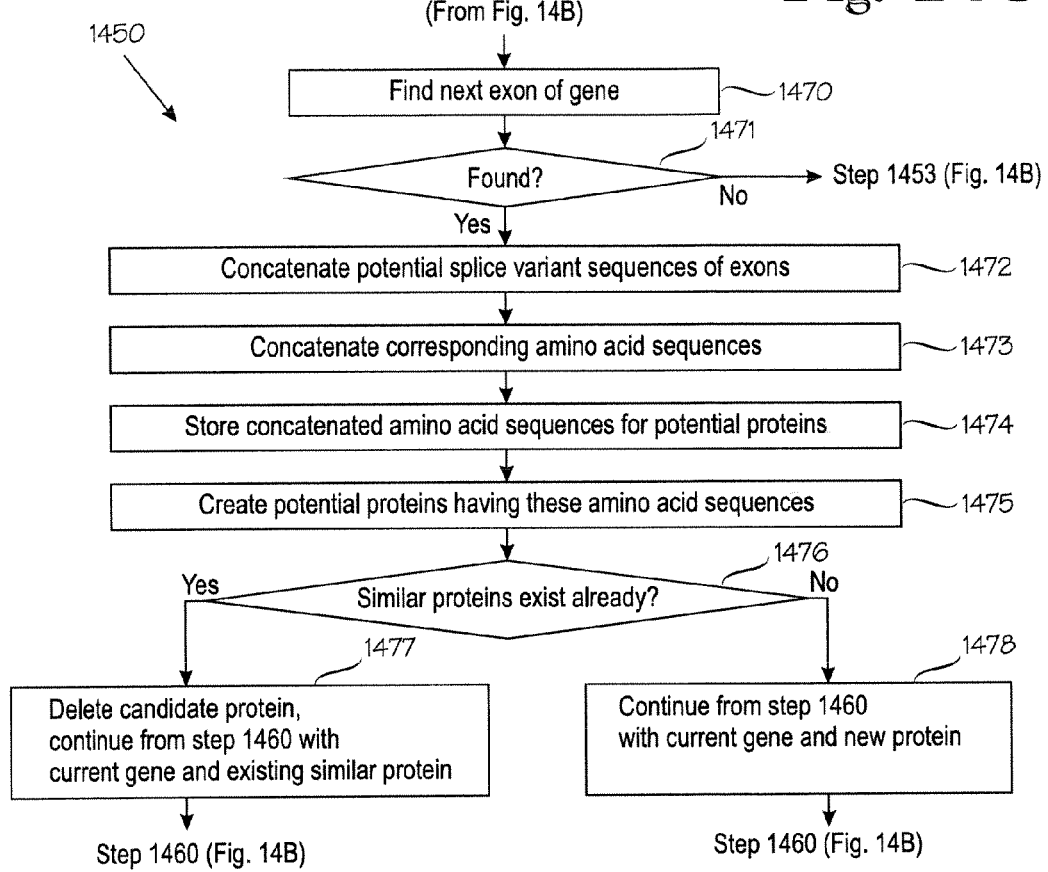

FIGS. 14B and 14C, which form a single logical drawing, illustrate a logic routine 1450 for automatically populating pathways from gene sequence databases that provide no explicit pathway information. The routine begins at step 1451 in which it takes as input the pathway name and the location name (the pathway to be populated) as well as the gene sequence files (eg EMBL flat files). In step 1452 the logic parses gene sequence data (eg EMBL FT lines) for creating exon records as follows:
Coding sequence annotation (TRUE/FALSE)
    Start point of exon (integer)
    End point of exon (integer)
    DNA sequence from start_point to end_point (string of acgt)
    Database reference of gene (eg based on EMBL/gene qualifier)
        database name (string eg EMBL)
        id_name (string eg/gene)
        id_string (string eg THBS3)
    Database reference of protein (eg based on EMBL db_xref)
        database name (string eg SWISS_PROT)
        id_name (string eg AC)
        id_string (string eg P49746)

In step 1453 the logic searches for the next gene from the exon records. If none is found, the process ends. In step 1455 the logic translates the database reference to a gene name via a database reference table (not shown separately). In step 1456 the logic searches for the next protein from the exon records related to the gene. If no proteins are found, the logic proceeds to step 1470. In step 1458, if no more proteins are found, the logic returns to step 1453. In step 1459 the logic translates the database reference to a protein name via a database reference table (not shown separately).

In step 1460 the logic checks if there are any transcripts connected between this gene and this protein in the pathway, such that the gene controls a transcription interaction AND the transcription interaction produces a transcript AND the transcript controls a translation interaction AND the translation interaction produces the protein. In step 1461, if any are found, the logic returns to step 1456. In steps 1462 to 1467, the logic creates pathway information as follows:
    transcript: mRNA_from_<gene name>_to_<protein name>
    interaction: mRNA_transcription_<gene name>_<protein name>
    interaction: translation_<protein name>
    control connection to the pathway: the gene controls the transcription
    product connection to the pathway: the transcription produces the transcript
    control connection to the pathway: the transcript controls a translation interaction
    product connection to the pathway: the translation interaction produces the protein In step 1468, some other biochemical entities (eg amino acids and ribosome) may optionally be connected to transcription and translation. Then the logic returns to step 1453. The steps shown in FIG. 14C are relevant if protein identifications are missing. In step 1470 the logic finds the next exon of the gene. If none are found, the logic returns to step 1453. In step 1472 the logic concatenates the potential splice variant sequences of the exons. In step 1473 the logic concatenates the corresponding amino acid sequences. In step 1474 the logic stores concatenated amino acid sequences for potential proteins. In step 1475 the logic creates potential proteins having these amino acid sequences. In step 1476 the logic checks if similar proteins have been stored in the database earlier. If yes, in step 1477, the logic delete the candidate protein and continues from step 1459 with the current gene and the existing similar protein. Otherwise, in step 1478, the logic continues from step 1459 with the current gene and the new protein. It should be noted that the pathway model described herein is capable of holding far more detailed information than what can be obtained from commercial gene sequence databases or the like. This means that the inventive pathway models can be only partially populated from commercial sequence databases. But considering the huge amount of biological data, even partial automatic population is better than completely manual population. Such partial automatic population is greatly facilitated by the fact that the pathway model described herein supports incomplete pathway information. The pathway model supports incomplete pathway information because the pathways are stored as systematic database relations between biochemical entities, interactions, locations, etc. In comparison, some prior art systems label pathway elements with simple text concatenations (such as "human_P53"). If further qualifiers are added to text concatenations, such as an identifier of a particular individual, entirely different labels are created (such as "human_12345_P53"), which destroys the integrity of a data base system.

Spatial Reference Models

Figure 15:
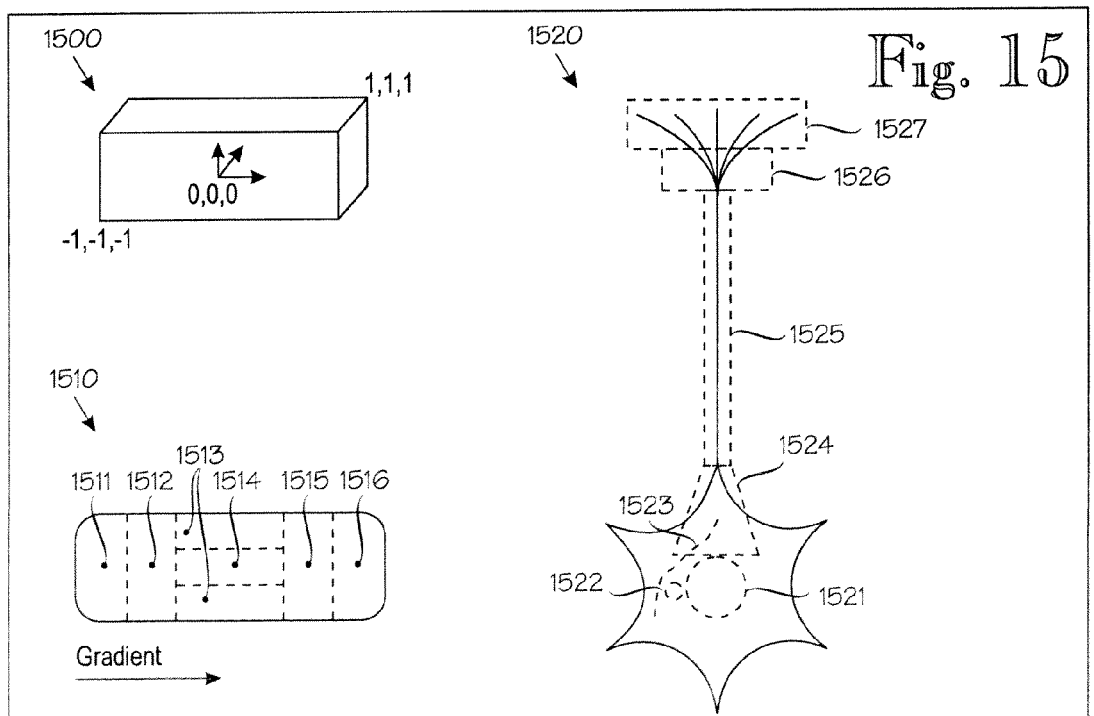
FIG. 15 illustrates spatial reference models for various cell types.

FIG. 15 illustrates spatial reference models for various cell types. It was stated earlier that a simple Cartesian or polar coordinate system may be sufficient for some cell types. The coordinate system is preferably normalized such that the maximum distance from a reference point is one.

There are many cell types for which a simple Cartesian or polar coordinate system is insufficient. For example, stem cells are directional, which means that they have a front end and a back end. Nerve cells are even more complex. Accordingly, the IMS preferably comprises several spatial reference models, and the spatial point is expressed as a combination of a reference model and an area within the reference model.

FIG. 15 shows three reference model examples. Reference model 1500 is a simple coordinate system, such as a three-dimensional Cartesian coordinate system. For some cell types, one or two coordinates may suffice. If the cell type in question has rotational symmetry, a polar coordinate system may be better than a Cartesian one.

Reference model 1510 is based on a division of a cell to several areas. The number of areas should be selected such that a piece of biochemical information is valid throughout the area. Reference model 1510 is suitable for a compact directional cell, such as a stem cell. The model 1510 is directional but rotationally symmetric. It has a front end area 1511, a rear end area 1516, a nucleus area 1514 and various intermediate areas 1512, 1513 and 1515. The front and rear ends can be selected relative to some gradient, such as a decreasing concentration of a compound.

Reference model 1520 is an example of modelling the topology of a nerve cell. It has a nucleus area 1521, various parts 1522, 1523 around the nucleus, a soma area 1524, an axon area 1525, etc. Normalized spatial coordinates can be used to increase detail level still further, if necessary. For instance, a point at the outer surface of an axon at its midpoint length-wise can be expressed {1520, 1525, (0.5, 1)}, wherein 1520 indicates the reference model, 1525 indicates the area within the reference model, 0.5 is a normalized length-wise coordinate along the axon and 1 means 100% of the radius along the cross section of the axon.

Pattern Matching

Figure 16C:
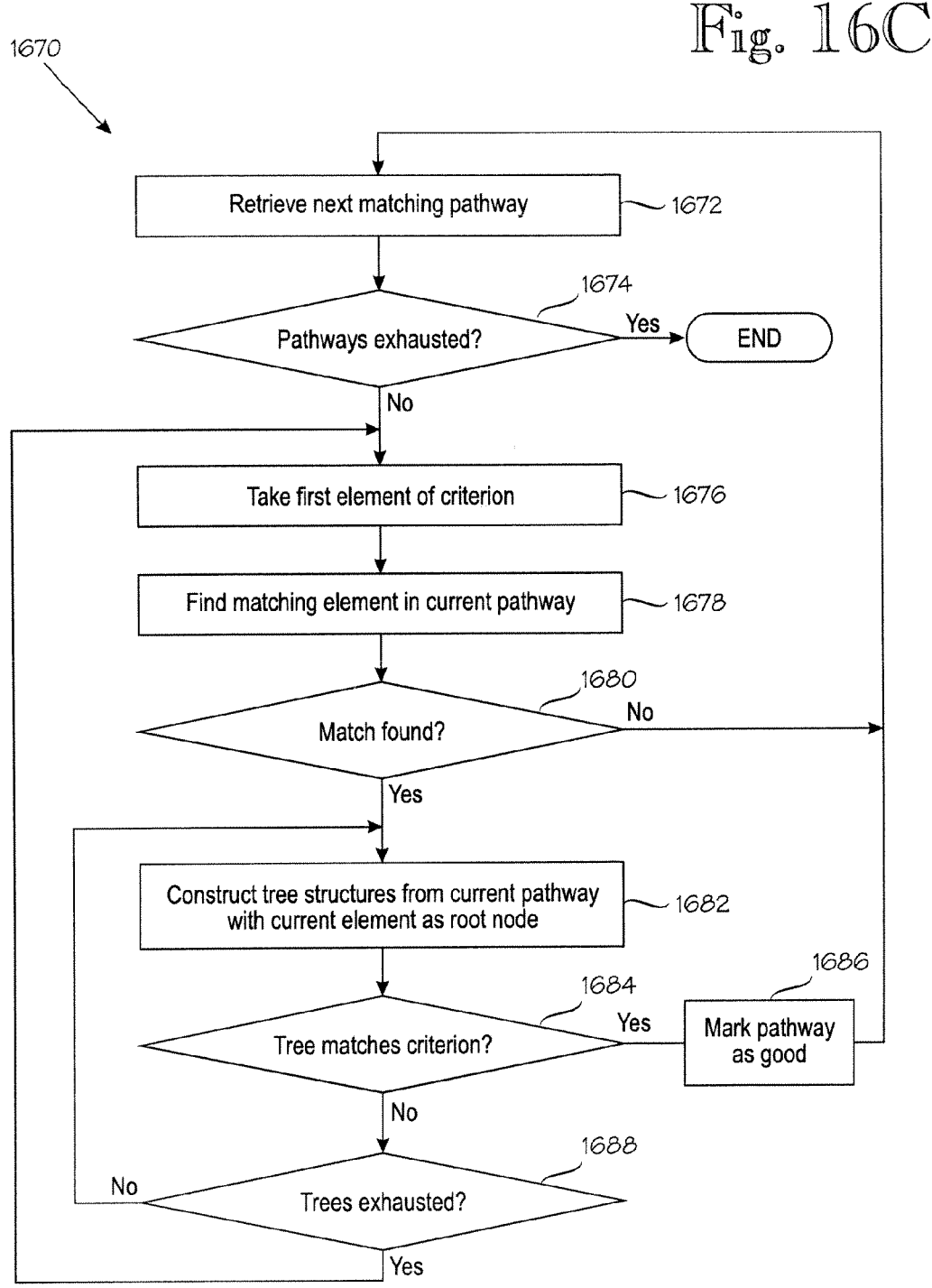

FIGS. 16A to 16C illustrate a technique for searching pathways that match a given pattern. According to a further preferred embodiment of the invention, the IMS comprises a pattern-matching logic that is able to search for topological patterns (pathway motifs). In pattern matching, the search criteria are relaxed and searches can be based on wildcards or gene ontologies, for example.

FIG. 16A illustrates an exemplary pathway that is a typical candidate for pattern matching. FIG. 16A uses the same drawing notation as FIG. 8. Reference numeral 1600 generally denotes a pathway that models self-inhibition, ie, a process in which a gene's expression is regulated by a product (protein) encoded by that gene. Pathway model 1600 models such a regulatory process as follows. Gene A 1602 has an "activates" 1604 relation to interaction B 1606. Interaction B 1606 has a "produces" relation 1608 to transcript C 1610, which in turn has an "activates" relation 1612 to interaction D 1614. Interaction D 1614 has a "produces" relation 1616 to protein E 1618, which closes causes the self-regulation by way of an "inhibits" relation 1620 to interaction B 1606.

FIG. 16B generally illustrates a pattern-matching logic 1650. Suppose that a researcher wishes to search the IMS for such self-regulation mechanisms. In order to support such searches, the IMS preferably comprises a pattern-matching logic 1650 that is arranged to carry out a wildcard search based on search criterion 1652 that may comprise wildcards. In this example, the search criterion 1652 is as follows:

G[*] activates I[*] produces Tr[*] activates I[*] produces P[*] inhibits @3

This example comprises two special symbols. The asterisks "*", denoted by reference signs 1652A, are wildcard expressions that match any character string. Such wildcard characters are will known in the field of information technology, but the use of such wildcard characters is only possible by virtue of the systematic way of storing biochemical information. The last term "@3", denoted by reference sign 1652B, is another special character and means the third term in the search criterion 1652, ie, the interaction I[*], which is activated (=second term) by any gene G[*] (=first term). The fact that the pattern-matching logic 1650 can process special terms like "@3" 1652B that refer to a previous term in the search criterion 1652, enables the pattern-matching logic 1650 to retrieve pathways that contain loops.

In addition to the search criterion 1652 that may comprise wildcards, the pattern-matching logic 1650 may have another input 1654 that indicates a list of potential pathways. The list may be an explicit list of specific pathways, or it may be an implicit list expressed as further search criteria based on elements of the pathway model (for potential search criteria, see FIGS. 7A to 8). As its output, the pattern-matching logic 1650 produces a list 1656 of pathways that match the search criterion 1652.

For example, the pattern-matching logic 1650 can be implemented as a recursive tree-search algorithm 1670 as shown in FIG. 16C. Step 1672 launches a database query that returns a list of pathways 1654 that matches the researcher's query parameters. For example, the query parameters may relate to the location 214, which is shown in more detail in FIG. 2, such that the location indicates a human liver. In step 1674, if no more matching pathways are found, the process ends. When a pathway is taken under study, the first element of the search criterion 1652 is selected in step 1676. In step 1678 a search is made in the current pathway for the next element that matches the first element of the search criterion. In step 1680, if the current pathway has no more elements that match the first element of criterion, the next pathway will be tried. In step 1682 tree structures are recursively constructed from the current pathway, taking the current element as the root node of the tree structure. In step 1684 it is tested whether the currently-tested tree structure matches the search criterion 1652. If yes, the current pathway is marked as a good one in step 1686. For example, the current pathway may be copied to the list of matching pathways 1656. If the current tree structure does not match the search criterion 1652, a test is made in step 1688 as to whether all tree structures from the current pathway element have been tried. If not, the process returns to step 1682, in which the next tree structure is constructed. If all tree structures from the current pathway element have been tried, the process returns to steps 1676-1678, in which the first element of the search criterion 1652 is again taken and another matching pathway element is tried as a root node for constructing candidates for matching tree structures, and so on.

As regards realization of step 1682, in which tree structures are constructed from the pathway under test, tree-search algorithms are disclosed in programming literature. In a normal tree-search algorithm, loops are normally not allowed, but in step 1682 a loop is allowed if that loop matches a loop in the search criterion 1652.

The example shown in FIG. 16B is based on textual wildcards. An even more capable system is achieved with ontology databases. This means that in step 1682 of FIG. 16C, the matching test is based on an ontology query instead of a wildcard match.

In the embodiment shown in FIGS. 16B and 16C, the search criterion (pathway pattern) was expressed in text form. It is also possible to enter a pathway pattern to be searched in the same way as pathways are generally entered into the IMS. FIG. 16A shows an example of a conventional pathway 1600, although in a real-life situation, the identifiers A through E will be replaced by actual identifiers of biochemical entities. FIG. 16D shows a pathway pattern (motif) 1660 that is structurally identical to the pathway 1600, but wildcards are substituted for some or all of the identifiers of biochemical entities. In this example, an identifier to the pathway pattern (motif) 1660 can be entered to the pattern-matching logic 1650 instead of the textual search criterion 1652.

FIG. 16E shows an exemplary SQL query 1690 for retrieving pathways that match the pathway pattern 1660. In this example the search criteria have been generated such that pathway_id=2 corresponds to pathway Pw[ . . . ] L[ . . . ]. The contents of the SQL query 1690 can be interpreted as follows. The SELECT sentence retrieves five id fields for values of variables C1_id through C5_id. The FROM clause specifies that the query is to retrieve from the connection table those connections whose id fields were requested in the SELECT sentence. The WHERE clause specifies the following conditions:

All connections must have pathway_id=2 (id for the pathway pattern);
Connection C1 is of type 3 (CONTROL);
Connection C2 is of type 3 (PRODUCT);
Connection C3 is of type 3 (CONTROL);
Connection C4 is of type 3 (PRODUCT);
Connection C5 is of type 3 (INHIBITION).

The object classes of the connections (gene, transcript, . . . ) are as follows:

Connections C1 and C3 have a common entity, so do C4 and C5;
Connections C1 and C2 have a common interaction;
Connections C3 and C4 have a common interaction;
Connections C5 and C1 have a common interaction;
Connections C5 and C2 have a common interaction.

When the query 1690 is processed, its result set indicates the pathways that meet the above criteria. In the retrieved pathways the pattern (motif) 1660 is easy to localize as soon as the five connections have been identified by means of their id fields.

Generation of the search criteria contains the following steps:
1. read connections of the pathway pattern (motif to search for);
2. based on their number, generate the SELECT sentence and FROM clause;
3. form the conditions of the WHERE clause based on the pathway pattern;
4. form the conditions for the types of the connections;
5. form the conditions for the object classes of the connections;
6. form the identity conditions for the biochemical entities joining the connections;
7. form the identity conditions for the interactions joining the connections.

If some of the entities in the pathway motif have been identified by a name of its own or by a GO class, the generation of the SQL query involves further conditions, wherein the name of the entity or the GO class connected by the annotation restricts entries to the result set.

Such a topological pattern matching by relatively simple database queries is greatly facilitated by the systematic pathway model described in connection with FIGS. 7A to 8 and the systematic variable description language described in connection with FIGS. 3A to 5.

It is readily apparent to a person skilled in the art that, as the technology advances, the inventive concept can be implemented in various ways. The invention and its embodiments are not limited to the examples described above but may vary within the scope of the claims.

Acronyms
IMS: Information Management System
VDL: Variable Description Language
SQL: Structured Query Language
XML: Extendible Markup Language

We claim:

1. An information management system (IMS) for managing biochemical information, the IMS comprising:
   a server and a database,
   means for storing in the database said biochemical information as variable data sets, wherein each variable data set comprises:
   a variable value matrix containing variable values organized as rows and columns;
   a row description list, in a variable description language, of the rows in the variable value matrix;
   a column description list, in the variable description language, of the columns in the variable value matrix; and
   a fixed dimension description, in the variable description language, of one or more fixed dimensions that are common to all values in the variable value matrix,
   wherein the server comprises a file system and the variable value matrix is addressable via the file system, independently of the row description list, column description list or fixed dimension description and the variable description language comprises variable expressions, each variable expression comprising one or more pairs of keyword and name; and the IMS further comprises a table having an entry for each permissible keyword, and the IMS further comprises means for storing compound variable expressions, each compound variable expression comprising two or more variable expressions separated by operators, functions or operators and functions.

2. The IMS of claim 1, further comprising a computer-implemented logic for performing a syntax check on variables expressed in said variable description language.

3. The IMS of claim 1, further comprising structured descriptions of biochemical pathways that are formed of at least pathways, biochemical entities, connections and interactions, wherein:
   each pathway has a relation to one or more connections;
   each connection joins one biochemical entity and one interaction; and
   each pathway has a relation to a specific location indication.

4. The IMS of claim 3, wherein each interaction has a relation to one or more kinetic laws.

5. An The IMS of claim 3, further comprising means for associating one of several predetermines roles to each connection, wherein the role indicates the role of the biochemical entity in the interaction and the several predetermines roles comprise substrate, product, activator and inhibitor.

6. The IMS of claim 3, further comprising means for associating a stoichiometric coefficient to each connection, wherein the stoichiometric coefficient indicates the number of molecules of the biochemical entity consumed or produced in the interaction.

7. The IMS of claim 3, further comprising a user interface logic for showing visualizations of said structured descriptions of biochemical pathways.

8. The IMS of claim 7, wherein the user interface logic comprises means for showing visualizations of measured or perturbated variables localized on the biochemical entities, interactions andlor connections of biochemical pathways.

9. The IMS of claim 3, further comprising pathway connections for combining several pathways to complex pathways.

10. The IMS of claim 1, further comprising a user interface logic for showing data traces between inter-related variable data sets.

11. The IMS of claim 1, wherein real-life biochemical entities and in-silico experiments are stored in structurally similar variable data sets.

12. A method for an information management system (IMS) managing biochemical information stored as variable data sets in a server which comprises a file system, wherein each variable data set comprises:
   a variable value matrix containing variable values organized as rows and columns;
   a row description list, in a variable description language, of the rows in the variable value matrix;
   a column description list, in the variable description language, of the columns in the variable value matrix; and
   a fixed dimension description, in the variable description language, of one or more fixed dimensions that are common to all values in the variable value matrix,
   wherein the server comprises a file system and the variable value matrix, the server performs column accessing via the file system, independently of the row description list, column description list or fixed dimension description and the variable description language comprises variable expressions, each variable expression comprising one or more pairs of keyword and name; and the IMS further comprises a table having an entry for each permissible keyword, and the IMS further performs storage of compound variable expressions, each compound variable expression comprising two or more variable expressions separated by operators, functions or operators and functions.

* * * * *